(12) United States Patent
Qin et al.

(10) Patent No.: US 9,700,044 B2
(45) Date of Patent: Jul. 11, 2017

(54) SYMMETRICAL MARINOPYRROLE DERIVATIVES AS POTENTIAL ANTIBIOTIC AGENTS

(71) Applicants: CHONGQING ZEIN PHARMACEUTICAL CO., LTD., Chongqing (CN); H. LEE MOFFITT CANCER CENTER AND RESEARCH INSTITUTE, INC., Tampa, FL (US)

(72) Inventors: Yong Qin, Chongqing (CN); Chunwei Cheng, Henan (CN); Hao Song, Sichuan (CN); Rongshi Li, Omaha, NE (US); Yan Liu, Omaha, NE (US)

(73) Assignees: H. Lee Moffitt Cancer Center and Research Institute, Inc., Tampa, FL (US); Chongqing Zein Pharmaceutical Co., Ltd., Chongqing (CN)

( * ) Notice: Subject to any disclaimer, the term of this patent is extended or adjusted under 35 U.S.C. 154(b) by 0 days.

(21) Appl. No.: 14/762,513

(22) PCT Filed: Jan. 22, 2014

(86) PCT No.: PCT/US2014/012442
§ 371 (c)(1),
(2) Date: Jul. 22, 2015

(87) PCT Pub. No.: WO2014/116634
PCT Pub. Date: Jul. 31, 2014

(65) Prior Publication Data
US 2015/0366197 A1    Dec. 24, 2015

Related U.S. Application Data

(60) Provisional application No. 61/755,021, filed on Jan. 22, 2013.

(51) Int. Cl.
*C07D 207/34* (2006.01)
*A01N 43/36* (2006.01)
*A61K 45/06* (2006.01)
*A61K 31/4025* (2006.01)
*C07D 207/14* (2006.01)

(52) U.S. Cl.
CPC .......... *A01N 43/36* (2013.01); *A61K 31/4025* (2013.01); *A61K 45/06* (2013.01); *C07D 207/14* (2013.01); *C07D 207/34* (2013.01)

(58) Field of Classification Search
CPC .............................. A01N 43/36; C07D 207/34
See application file for complete search history.

(56) References Cited

U.S. PATENT DOCUMENTS

| 4,559,157 A | 12/1985 | Smith et al. |
| 4,608,392 A | 8/1986 | Jacquet et al. |
| 4,820,508 A | 4/1989 | Wortzman |
| 4,992,478 A | 2/1991 | Geria |
| 6,468,953 B1 | 10/2002 | Hitchems et al. |
| 2015/0080632 A1* | 3/2015 | Li et al. ............................ 600/1 |

FOREIGN PATENT DOCUMENTS

| WO | 2011/103788 | 2/2011 |
| WO | 2014/116634 | 7/2014 |

OTHER PUBLICATIONS

Acoca, S., et al., "Molecular dynamics study of small molecule inhibitors of the Bcl-2 family," Proteins, vol. 79, 2011, pp. 2624-2636.
Albershardt, T.C., et al., "Multiple BH3 Mimetics Antagonize Antiapoptotic MCL1 Protein by Inducing the Endoplasmic Reticulum Stress Response and Up-regulating BH3-only Protein NOXA," The Journal of Biological Chemistry, vol. 286, No. 28, 2011, pp. 24882-24895.
Beroukhim, R., et al., "The landscape of somatic copy-number alteration across human cancers," Nature, vol. 463, 2010, pp. 899-905.
Bhat, U.G., et al., "ARC Synergizes with ABT-737 to Induce Apoptosis in Human Cancer Cells," Molecular Cancer Therapeutics, vol. 9, 2010, pp. 1688-1696.
Butler, K.V., et al., "Rational Design and Simple Chemistry Yield a Superior, Neuroprotective HDAC6 Inhibitor, Tubastatin A," Journal of the American Chemical Society, vol. 132, 2010, pp. 10842-10846.
Chen, S., et al., "Mcl-1 Down-regulation Potentiates ABT-737 Lethality by Cooperatively Inducing Bak Activation and Bax Translocation," Cancer Research, vol. 67, 2007, pp. 782-791.
Cheng, C., et al., "Total Synthesis of (±)-Marinopyrrole A and Its Library as Potential Antibiotic and Anticancer Agents," Journal of Combinatorial Science, vol. 12, No. 4, 2010, pp. 541-547.
Czabotar, P.E., et al., "Structural insights into the degradation of Mcl-1induced by BH3 domains," Proceedings of the National Academy of Sciences, vol. 104, 2007, pp. 6217-6222.
Day, C.L., et al., "Structure of the BH3 Domains from the p53-Inducible BH3-Only Proteins Noxa and Puma in Complex with Mcl-1," Journal of Molecular Biology, vol. 380, 2008, pp. 958-971.
Domina, A.M., et al., "MCL1 is phosphorylated in the PEST region and stabilized upon ERK activation in viable cells, and at additional sites with cytotoxic okadaic acid or taxol," Oncogene, vol. 23, 2004, pp. 5301-5315.
Eldridge, M.D., et al., "Empirical scoring functions: I. The development of a fast empirical scoring function to estimate the binding affinity of ligands in receptor complexes," Journal of Computer-Aided Molecular Design, vol. 11, 1997, pp. 425-445.

(Continued)

*Primary Examiner* — Rebecca Anderson
*Assistant Examiner* — Karen Cheng
(74) *Attorney, Agent, or Firm* — Meunier Carlin & Curfman LLC

(57) ABSTRACT

Symmetrical marinopyrrole derivatives are disclosed herein, as is a synthetic route for producing these compounds. Also disclosed are methods of using symmetrical marinopyrrole derivatives to treat bacterial pathogens, like MRSE, MSSA and MRSA.

14 Claims, No Drawings

(56) References Cited

OTHER PUBLICATIONS

Facchetti, F., et al., "Modulation of pro- and anti-apoptotic factors in human melanoma cells exposed to histone deacetylase inhibitors," Apoptosis, vol. 9, 2004, pp. 573-582.

Fournel, M., et al., "MGCD0103, A novel isotype-selective histone deacetylase inhibitor, has broad spectrum antitumor activity in vitro and in vivo," Molecular Cancer Therapeutics, vol. 7, 2008, pp. 759-768.

Friesner, R.A., et al., "Glide: A New Approach for Rapid, Accurate Docking and Scoring. I. Method and assessment of Docking Accuracy," Journal of Medicinal Chemistry, vol. 47, 2004, pp. 1739-1749.

Furneaux, R.H., et al., "Improved Syntheses of 3H,5H-Pyrrolo [3,2-d] pyrimidines," The Journal of Organic Chemistry, vol. 64, 1999, pp. 8411-8412.

Gao, L., et al., "Cloning and Functional Characterization of HDAC11, a Novel Member of the Human Histone Deacetylase Family," The Journal of Biological Chemistry, vol. 277, No. 28, 2002, pp. 25748-25755.

Gomez-Bougie, P., et al., "Noxa controls Mule-dependent Mcl-1 ubiquitination through the regulation of the Mcl-1/USP9X interaction," Biochemical and Biophysical Research Communications, vol. 413, 2011, pp. 460-464.

Guo, D., et al., "Efficient Iron-Catalyzed N-Arylation of Aryl Halides with Amines," Organic Letters, vol. 10, No. 20, 2008, pp. 4513-4516.

Haste, N.M., et al., Pharmacological Properties of the Marine Natural Product Marinopyrrole A against Methicillin-Resistant *Staphylococcus aureus*, Antimicrobial Agents and Chemotherapy, vol. 55, No. 7, 2011, pp. 3305-3312.

Hikita, H., et al., "The Bcl-xL Inhibitor, ABT-737, Efficiently Induces Apoptosis and Suppresses Growth of Hepatoma Cells in Combination with Sorafenib," Hepatology, vol. 52, No. 4, 2010, pp. 1310-1321.

Hu, X., et al., "Bcl-$X_L$-templated assembly of its own protein-protein interaction modulator from fragments decorated with thio acids and sulfonyl azides," Journal of the American Chemical Society, vol. 130, No. 42, 2008, pp. 13820-13821.

Hughes, C.C., et al., "Marinopyrrole A Target Elucidation by Acyl Dye Transfer," Journal of the American Chemical Society, vol. 131, No. 34, 2009, pp. 12094-12096.

Hughes, C.C., et al., Structures, Reactivities, and Antibiotic Properties of the Marinopyrroles A-F, Journal of Organic Chemistry, vol. 75, 2010, pp. 3240-3250.

Hughes, C.C., et al., The Marinopyrroles, Antibiotics of an Unprecedented Structure Class from a Marine *Streptomyces* sp., Organic Letters, vol. 10, No. 4, 2008, pp. 629-631.

Ji, M., et al., "Simultaneous targeting of *MCL1* and *ABCB1* as a novel strategy to overcome drug resistance in human leukaemia," British Journal of Haematology, vol. 145, 2009, pp. 648-656.

Jorgensen, W.L., et al., "Development and Testing of the OPLS All-Atom Force Field on Conformational Energetics and Properties of Organic Liquids," Journal of the American Chemical Society, vol. 118, 1996, pp. 11225-11236.

Kalin, K.H., et al., "Second-Generation Histone Deacetylase 6 Inhibitors Enhance the Immunosuppressive Effects of Foxp3+ T-Regulatory Cells," Journal of Medicinal Chemistry, vol. 55, 2012, pp. 639-651.

Kanakis, A.A., et al., "Total Synthesis of (±)—Marinopyrrole A via Copper-Mediated N-Arylation," Organic Letters, vol. 12, No. 21, 2010, pp. 4872-4875.

Kazi, A., et al., "The BH3 α-Helical Mimic BH3-M6 Disrupts Bcl-$X_L$, Bcl-2, and MCL-1 Protein-Protein Interactions with Bax, Bak, Bad, or Bim and Induces Apoptosis in a Bax-and Bim-dependent Manner," The Journal of Biological Chemistry, vol. 286, No. 11, 2011, pp. 9382-9392.

Kelly, W.K., et al., "Drug Insight: histone deacetylase inhibitors—development of the new targeted anticancer agent suberoylanilide hydroxamic acid," Nature Clinical Practice Oncology, vol. 2, No. 3, 2005, pp. 150-157.

Konopleva, M., et al. "Mechanisms of apoptosis sensitivity and resistance to the BH3 mimetic ABT-737 in acute myeloid leukemia," Cancer Cell, vol. 10, 2006, pp. 375-388.

Krajewska, M., et al., Immunohistochemical Analysis of in Vivo Patterns of Expression of CPP32 (Caspase-3), a Cell Death Protease, Cancer Research, vol. 57, 1997, pp. 1605-1613.

Krajewski, S., et al., "Immunohistochemical Analysis of Mcl-1 and Bcl-2 Proteins in Normal and Neoplastic Lymph Nodes," American Journal of Pathology, vol. 145, No. 3, 1994, pp. 515-525.

Kwong, F.Y., et al, "Copper-catalyzed coupling of alkylamines and aryl iodides: An efficient system even in an air atmosphere," Organic Letters, vol. 4, 2002, pp. 581-584.

Li, R., et al., "Design, synthesis and evaluation of marinopyrrole derivatives as selective inhibitors of Mcl-1 binding to pro-apoptotic Bim and dual Mcl-1/Bcl-xL inhibitors," European Journal of Medicinal Chemistry, vol. 90, 2015, pp. 315-331.

Liao, A., et al., "Therapeutic efficacy of FTY720 in a rat model of NK-cell leukemia," Blood, vol. 118, No. 10, 2011, pp. 2793-2800.

Lin, X., et al., "'Seed' analysis of off-target siRNAs reveals an essential role of Mcl-1 in resistance to the small-molecule Bcl-2/Bcl-$X_L$ inhibitor ABT-737," Oncogene, vol. 26, 2007, pp. 3972-3979.

Maurer, U., et al., Glycogen Synthase Kinase-3 Regulates Mitochondrial Outer Membrane Permeabilization and Apoptosis by Destabilization of MCL-1, Molecular Cell, vol. 21, 2006, pp. 749-760.

Nguyen, M., et al., "Small molecule obatoclax (GX15-070) antagonizes MCL-1 and overcomes MCL-1-mediated resistance to apoptosis," Proceedings of the National Academy of Sciences, vol. 104, No. 49, 2007, pp. 19512-19517.

Nicolaou, K.C., et al., "Total synthesis and biological evaluation of marinopyrrole A and analogs," Tetrahedron Letters, vol. 52, No. 17, 2011, pp. 2041-2043.

Okano, K., et al., "Synthesis of Secondary Arylamines through Copper-Mediated Intermolecular Aryl Amination," Organic Letters, vol. 5, No. 26, 2003, pp. 4987-4990.

Oltersdorf, T., et al., "An inhibitor of Bcl-2 family proteins induces regression of solid tumours," Nature, vol. 435, 2005, pp. 677-681.

Paremigiani, R.B., et al., "HDAC6 is a specific deacetylase of peroxiredoxins and is involved in redox regulation," Proceedings of the National Academy of Sciences, vol. 105, No. 28, 2008, pp. 9633-9638.

Quinn, B.A., et al., "Targeting Mcl-1 for the therapy of cancer," Expert Opinion on Investigational Drugs, vol. 20, No. 10, 2011, pp. 1397-1411.

Reed, J.C., et al., "BCL-2 Family Proteins: Regulators of Cell Death Involved in the Pathogenesis of Cancer and Resistance to Therapy," Journal of Cellular Biochemistry, vol. 60, 1996, pp. 23-32.

Reed, J.C., et al., Bcl-2 Family Proteins: Strategies for Overcoming Chemoresistance in Cancer, Advances in Pharmacology, vol. 41, 1997, pp. 501-532.

Rochais, C., et al., "Synthesis and biological evaluation of novel pyrrolopyrrolizinones as anticancer agents," Bioorganic & Medicinal Chemistry, vol. 14, 2006, pp. 8162-8175.

Santo, L., et al., "Preclinical activity, pharmacodynamic, and pharmacokinetic properties of a selective HDAC6 inhibitor, ACY-1215, in combination with bortezomib in multiple myeloma," Blood, vol. 119, 2012, pp. 2579-2589.

Sattler, M., et al., Structure of Bcl-$x_L$-Bak Peptide Complex: Recognition Between Regulators of Apoptosis, Science, vol. 275, 1997, pp. 983-986.

Stewart, M.L., et al., "The MCL-1 BH3 helix is an exclusive MCL-1 inhibitor and apoptosis sensitizer," Nature Chemical Biology, vol. 6, 2010, pp. 595-601.

Tahir, S.K., et al., "Influence of Bcl-2 Family Members on the Cellular Response of Small-Cell Lung Cancer Cell Lines to ABT-737," Cancer Research, vol. 67, 2007, pp. 1176-1183.

(56) References Cited

OTHER PUBLICATIONS

Tse, C., et al., "ABT-263: A Potent and Orally Bioavailable Bcl-2 Family Inhibitor," Cancer Research, vol. 68, No. 9, 2008, pp. 3421-3428.
Van Delft, M.F., et al., "The BH3 mimetic ABT-737 targets selective Bcl-2 proteins and efficiently induces apoptosis via Bak/Bax if Mcl-1 is neutralized," Cancer Cell, vol. 10, 2006, pp. 389-399.
Vickers, C.J., et al., "Discovery of HDAC Inhibitors That Lack an Active Site $Zn^{2+}$-Binding Functional Group," ACS Medicinal Chemistry Letters, vol. 3, 2012, pp. 505-508.
Villagra, A., et al., "The histone deacetylase HDAC11 regulates the expression of interleukin 10 and immune tolerance," Nature Immunology, vol. 10, No. 1, 2009, pp. 92-100.
Vogler, M. et al., "Bcl-2 inhibitors: small molecules with a big impact on cancer therapy," Cell Death and Differentiation, vol. 16, 2009, pp. 360-367.
Wagner, J.M., et al., "Histone deacetylase (HDAC) inhibitors in recent clinical trials for cancer therapy," Clinical Epigenetics, vol. 1, 2010, pp. 117-136.
Wang, G-Q, et al., "A Role for Mitochondrial Bak in Apoptotic Response to Anticancer Drugs," The Journal of Biological Chemistry, vol. 276, 2001, pp. 34307-34317.
Wang, H., et al., "Histone Deacetylase Inhibitor LAQ824 Augments Inflammatory Responses in Macrophages through Transcriptional Regulation of IL-10," The Journal of Immunology, vol. 186, 2011, pp. 3986-3996.
Willis, S.N., et al., Proapoptotic Bak is sequestered by Mcl-1 and Bcl-xL, but not Bcl-2, until displaced by BH3-only proteins, Genes Dev 19:1294-1305, 2005.
Woods, N.T., et al., "Anoikis, Initiated by Mcl-1 Degradation and Bim Induction, Is Deregulated during Oncogenesis," Cancer Research, vol. 67, No. 22, 2007, pp. 10744-10752.
Wuilléme-Toumi, S., et al., "Reciprocal protection of Mcl-1 and Bim from ubiquitin-proteasome degradation," Biochemical and Biophysical Research Communications, vol. 361, 2007, pp. 865-869.
Yecies, D., et al., "Acquired resistance to ABT-737 in lymphoma cells that up-regulate MCL-1 and BFL-1," Blood, vol. 115, 2010, pp. 3304-3313.
Yip, K.W., et al., "Bcl-2 family proteins and cancer," Oncogene, 2008, vol. 27, pp. 6398-6406.
Zhang, Y., et al., "Mice Lacking Histone Deacetylase 6 Have Hyperacetylated Tubulin but are Viable and Develop Normally," Molecular and Cellular Biology, vol. 28, 2008, pp. 1688-1701.
Zhou, N., et al., "Discovery of N-(2-Aminophenyl)-4-[4-pyridin-3-ylpyrimidin-2-ylamino)methyl]benzamide (MGCD0103), an Orally Active Histone Deacetylase Inhibitor," Journal of Medicinal Chemistry, vol. 51, 2008, pp. 4072-4075.
Zou, H., et al., "Characterization of the two catalytic domains in histone deacetylase 6," Biochemical and Biophysical Research Communications, vol. 341, 2006, pp. 45-50.
International Preliminary Report on Patentability and Written Opinion, dated Oct. 21, 2014, received in connection with International Patent Application No. PCT/US2013/024424.
International Search Report and Written Opinion, dated Jun. 2, 2013, received in connection with International Patent Application No. PCT/US2013/024424.
International Preliminary Report on Patentability and Written Opinion, dated Jul. 28, 2015, received in connection with International Patent Application No. PCT/US2014/012442.
International Search Report, dated Apr. 30, 2014, received in connection with International Patent Application No. PCT/US2014/012442.
Non-final Office Action, dated Jun. 26, 2015, received in connection with U.S. Appl. No. 14/394,902.
Notice of Allowance for U.S. Appl. No. 14/394,902 issued Mar. 30, 2016.

* cited by examiner

SYMMETRICAL MARINOPYRROLE DERIVATIVES AS POTENTIAL ANTIBIOTIC AGENTS

CROSS REFERENCE TO RELATED APPLICATIONS

This application claims the benefit of priority to U.S. Provisional Application 61/755,021, filed Jan. 22, 2013, which is incorporated by reference herein in its entirety.

BACKGROUND

Marinopyrroles were first reported to show antibiotic activity against methicillin-resistant *Staphylococcus aureus* (MRSA) in 2008 (Hughes et al., "The marinopyrroles, antibiotics of an unprecedented structure class from a marine *Streptomyces* sp." *Org Lett* 10:629-631, 2008). Due to their novel class of molecular structures and promising biological properties, the marinopyrroles have attracted considerable attention. The first total synthesis of (±)-marinopyrrole A was reported along with 12 derivatives in early 2010 (Cheng et al., "Total synthesis of (±)-marinopyrrole A and its library as potential antibiotic and anticancer agents," *J Comb Chem* 12:541-547, 2010). Synthesis of (±)-marinopyrrole A via an intermolecular Ullman coupling reaction as a key step to form bispyrrole system was published by Kanakis and Sarli five months later (Kanakis et al., "Total synthesis of (±)-marinopyrrole A via copper-mediated N-arylation," *Org Lett* 12:4872-4875, 2010). In 2011, Nicolaou's group published a new five-step method to access marinopyrrole derivatives as well as (+)- and (−)-atropisomer after a chiral separation of (±)-marinopyrrole A using chiral HPLC and their antibiotic activities against MRSA (Nicolaou et al., "Total synthesis and biological evaluation of marinopyrrole A and analogues," *Tet Lett* 52:2041-2043, 2011). Recently, the synthesis of a novel series of "asymmetrical" marinopyrrole derivatives with superior antibiotic activities against MRSA to that of the parent marinopyrrole A was revealed (Liu et al., "Marinopyrrole derivatives as potential antibiotic agents against methicillin-resistant *Staphylococcus aureus* (I)," *Mar Drugs* 10:953-962, 2012). Most recently, Moore's group published biosynthesis of marinopyrrole A via a N,C-bipyrrole homocoupling catalyzed by two flavin-dependent halogenases (Yamanaka et al., "Flavoenzyme-catalyzed atropo-selective n,c-bipyrrole homocoupling in marinopyrrole biosynthesis," *J Am Chem Soc* 134:12434-12437, 2012).

The global crisis of antibiotic resistance has spread rapidly over the last several decades. MRSA infections have reached epidemic proportions in many countries and represent the most common cause of skin and soft tissue infections in the United States (Grundmann et al., "Emergence and resurgence of methicillin-resistant *Staphylococcus aureus* as a public-health threat," *Lancet* 368:874-885, 2006; Como-Sabetti et al., "Community-associated methicillin-resistant *Staphylococcus aureus*: trends in case and isolate characteristics from six years of prospective surveillance," *Public Health Rep* 124:427-435, 2009). Both hospital-associated and community-associated MRSA can exhibit broader resistance to multiple classes of antibiotics (Chambers et al., "Waves of resistance: *Staphylococcus aureus* in the antibiotic era," *Nat Rev Microbiol* 7:629-641, 2009; Deleo et al., "Community-associated methicillin-resistant *Staphylococcus aureus*," *Lancet* 375:1557-1568, 2010; Lowy, "Antimicrobial resistance: the example of *Staphylococcus aureus*," *J Clin Invest* 111:1265-1273, 2003). Hospital-associated MRSA infections are common among healthcare facilities and are resistant to many antibiotics. However, community-associated MRSA strains are highly virulent and infect even healthy individuals; the incidence of these infections has skyrocketed in the last decade. The relative abandonment of antibiotic discovery and development by the pharmaceutical industry has created a vacuum in the introduction of new antibiotics to treat these increasingly problematic infections. Except for the addition of the oxazolidinone linezolid in 2000, the lipopeptide daptomycin in 2003, and FDA's recent approval of ceftaroline (Teflaro) as an injectable antibiotic to treat adults with community acquired bacterial pneumonia and acute bacterial skin and skin structure infections including MRSA, a very limited number of new antibiotics have been discovered over the last half a century, with only two new classes of anti-MRSA drugs having been approved in the last 40 years. Clearly, novel agents for the treatment of MRSA infections are urgently needed (Butler et al., "Natural products—the future scaffolds for novel antibiotics?" *Biochem Pharmacol* 71:919-929, 2006). The compositions and methods disclosed herein address these and other needs.

SUMMARY

In accordance with the purposes of the disclosed materials, compounds, compositions, kits, and methods, as embodied and broadly described herein, the disclosed subject matter relates to compositions, methods of making said compositions, and methods of using said compositions. More specifically, symmetrical marinopyrrole derivatives that can be used as antibacterial agents are disclosed herein. In specific aspects, the disclosed subject matter relates to antibacterial compounds. More specifically, the subject matter disclosed herein relates to symmetrical marinopyrrole derivatives and their use in the treatment of bacterial infections, such as methicillin-resistant *Staphylococcus aureus* (MRSA). Still further, the disclosed subject matter relates to symmetrical marinopyrrole derivatives and their use in the treatment of MRSA, even in the presence of human serum.

Additional advantages will be set forth in part in the description that follows or may be learned by practice of the aspects described below. The advantages described below will be realized and attained by means of the elements and combinations particularly pointed out in the appended claims. It is to be understood that both the foregoing general description and the following detailed description are exemplary and explanatory only and are not restrictive.

DETAILED DESCRIPTION

The materials, compounds, compositions, articles, and methods described herein may be understood more readily by reference to the following detailed description of specific aspects of the disclosed subject matter and the Examples included therein.

Before the present materials, compounds, compositions, kits, and methods are disclosed and described, it is to be understood that the aspects described below are not limited to specific synthetic methods or specific reagents, as such may, of course, vary. It is also to be understood that the terminology used herein is for the purpose of describing particular aspects only and is not intended to be limiting.

Also, throughout this specification, various publications are referenced. The disclosures of these publications in their entireties are hereby incorporated by reference into this application in order to more fully describe the state of the art to which the disclosed matter pertains. The references disclosed are also individually and specifically incorporated by reference herein for the material contained in them that is discussed in the sentence in which the reference is relied upon.

GENERAL DEFINITIONS

In this specification and in the claims that follow, reference will be made to a number of terms, which shall be defined to have the following meanings:

Throughout the description and claims of this specification the word "comprise" and other forms of the word, such as "comprising" and "comprises," means including but not limited to, and is not intended to exclude, for example, other additives, components, integers, or steps.

As used in the description and the appended claims, the singular forms "a," "an," and "the" include plural referents unless the context clearly dictates otherwise. Thus, for example, reference to "a composition" includes mixtures of two or more such compositions, reference to "the compound" includes mixtures of two or more such compounds, and the like.

"Optional" or "optionally" means that the subsequently described event or circumstance can or cannot occur, and that the description includes instances where the event or circumstance occurs and instances where it does not.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. Unless stated to the contrary the term "about" means ±5% of a value, for example, ±4, 3, 2, or 1% of a value. Also, if the value "10" is disclosed, then "about 10" is also disclosed. It is also understood that when a value is disclosed, then "less than or equal to" the value, "greater than or equal to the value," and possible ranges between values are also disclosed, as appropriately understood by the skilled artisan. For example, if the value "10" is disclosed, then "less than or equal to 10" as well as "greater than or equal to 10" is also disclosed. It is also understood that throughout the application data are provided in a number of different formats and that this data represent endpoints and starting points and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

As used herein, by a "subject" is meant an individual. Thus, the "subject" can include domesticated animals (e.g., cats, dogs, etc.), livestock (e.g., cattle, horses, pigs, sheep, goats, etc.), laboratory animals (e.g., mouse, rabbit, rat, guinea pig, etc.), and birds. "Subject" can also include a mammal, such as a primate or a human.

By "reduce" or other forms of the word, such as "reducing" or "reduction," is meant lowering of an event or characteristic (e.g., bacterial growth). It is understood that this is typically in relation to some standard or expected value, in other words it is relative, but that it is not always necessary for the standard or relative value to be referred to. For example, "reduces bacterial infection" means reducing the spread of a bacterial infection relative to a standard or a control.

By "prevent" or other forms of the word, such as "preventing" or "prevention," is meant to stop a particular event or characteristic, to stabilize or delay the development or progression of a particular event or characteristic, or to minimize the chances that a particular event or characteristic will occur. Prevent does not require comparison to a control as it is typically more absolute than, for example, reduce. As used herein, something could be reduced but not prevented, but something that is reduced could also be prevented. Likewise, something could be prevented but not reduced, but something that is prevented could also be reduced. It is understood that where reduce or prevent are used, unless specifically indicated otherwise, the use of the other word is also expressly disclosed.

By "treat" or other forms of the word, such as "treated" or "treatment," is meant to administer a composition or to perform a method in order to reduce, prevent, or eliminate a particular characteristic or event (e.g., bacterial growth). The term "control" is used synonymously with the term "treat."

By "antimicrobial" is meant the ability to treat or control (e.g., reduce, prevent, or eliminate) the growth of a microbe at any concentration. Similarly, the term "antibacterial" refers to the ability to treat or control cellular bacteria growth at any concentration.

It is understood that throughout this specification the identifiers "first" and "second" are used solely to aid in distinguishing the various components and steps of the disclosed subject matter. The identifiers "first" and "second" are not intended to imply any particular order, amount, preference, or importance to the components or steps modified by these terms.

CHEMICAL DEFINITIONS

As used herein, the term "substituted" is contemplated to include all permissible substituents of organic compounds. In a broad aspect, the permissible substituents include acyclic and cyclic, branched and unbranched, carbocyclic and heterocyclic, and aromatic and nonaromatic substituents of organic compounds. Illustrative substituents include, for example, those described below. The permissible substituents can be one or more and the same or different for appropriate organic compounds. For purposes of this disclosure, the heteroatoms, such as nitrogen, can have hydrogen substituents and/or any permissible substituents of organic compounds described herein which satisfy the valencies of the heteroatoms. This disclosure is not intended to be limited in any manner by the permissible substituents of organic compounds.

Also, the terms "substitution" or "substituted with" include the implicit proviso that such substitution is in accordance with permitted valence of the substituted atom and the substituent, and that the substitution results in a stable compound, e.g., a compound that does not spontaneously undergo transformation such as by rearrangement, cyclization, elimination, etc.

"$Z^1$," "$Z^2$," "$Z^3$," and "$Z^4$" are used herein as generic symbols to represent various specific substituents. These symbols can be any substituent, not limited to those disclosed herein, and when they are defined to be certain substituents in one instance, they can, in another instance, be defined as some other substituents.

The term "aliphatic" as used herein refers to a non-aromatic hydrocarbon group and includes branched and unbranched, alkyl, alkenyl, or alkynyl groups.

The term "alkyl" as used herein is a branched or unbranched saturated hydrocarbon group of 1 to 24 carbon atoms, such as methyl, ethyl, n-propyl, isopropyl, n-butyl, isobutyl, t-butyl, pentyl, hexyl, heptyl, octyl, nonyl, decyl, dodecyl, tetradecyl, hexadecyl, eicosyl, tetracosyl, and the like. The alkyl group can also be substituted or unsubstituted. The alkyl group can be substituted with one or more groups including, but not limited to, alkyl, halogenated alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol, as described below.

Throughout the specification "alkyl" is generally used to refer to both unsubstituted alkyl groups and substituted alkyl groups; however, substituted alkyl groups are also specifically referred to herein by identifying the specific substituent(s) on the alkyl group. For example, the term "halogenated alkyl" specifically refers to an alkyl group that is substituted with one or more halide, e.g., fluorine, chlorine, bromine, or iodine. The term "alkoxyalkyl" specifically refers to an alkyl group that is substituted with one or more alkoxy groups, as described below. The term "alkylamino" specifically refers to an alkyl group that is substituted with one or more amino groups, as described below, and the like. When "alkyl" is used in one instance and a specific term such as "alkylalcohol" is used in another, it is not meant to imply that the term "alkyl" does not also refer to specific terms such as "alkylalcohol" and the like.

This practice is also used for other groups described herein. That is, while a term such as "cycloalkyl" refers to both unsubstituted and substituted cycloalkyl moieties, the substituted moieties can, in addition, be specifically identified herein; for example, a particular substituted cycloalkyl can be referred to as, e.g., an "alkylcycloalkyl." Similarly, a substituted alkoxy can be specifically referred to as, e.g., a "halogenated alkoxy," a particular substituted alkenyl can be, e.g., an "alkenylalcohol," and the like. Again, the practice of using a general term, such as "cycloalkyl," and a specific term, such as "alkylcycloalkyl," is not meant to imply that the general term does not also include the specific term.

The term "alkoxy" as used herein is an alkyl group bound through a single, terminal ether linkage; that is, an "alkoxy" group can be defined as $-OZ^1$ where $Z^1$ is alkyl as defined above.

The term "alkenyl" as used herein is a hydrocarbon group of from 2 to 24 carbon atoms with a structural formula containing at least one carbon-carbon double bond. Asymmetric structures such as $(Z^1Z^2)C=C(Z^3Z^4)$ are intended to include both the E and Z isomers. This can be presumed in structural formulae herein wherein an asymmetric alkene is present, or it can be explicitly indicated by the bond symbol C=C. The alkenyl group can be substituted with one or more groups including, but not limited to, alkyl, halogenated alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol, as described below.

The term "alkynyl" as used herein is a hydrocarbon group of 2 to 24 carbon atoms with a structural formula containing at least one carbon-carbon triple bond. The alkynyl group can be substituted with one or more groups including, but not limited to, alkyl, halogenated alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol, as described below.

The term "aryl" as used herein is a group that contains any carbon-based aromatic group including, but not limited to, benzene, naphthalene, phenyl, biphenyl, phenoxybenzene, and the like. The term "heteroaryl" is defined as a group that contains an aromatic group that has at least one heteroatom incorporated within the ring of the aromatic group. Examples of heteroatoms include, but are not limited to, nitrogen, oxygen, sulfur, and phosphorus. The term "non-heteroaryl," which is included in the term "aryl," defines a group that contains an aromatic group that does not contain a heteroatom. The aryl or heteroaryl group can be substituted or unsubstituted. The aryl or heteroaryl group can be substituted with one or more groups including, but not limited to, alkyl, halogenated alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol as described herein. The term "biaryl" is a specific type of aryl group and is included in the definition of aryl. Biaryl refers to two aryl groups that are bound together via a fused ring structure, as in naphthalene, or are attached via one or more carbon-carbon bonds, as in biphenyl.

The term "cycloalkyl" as used herein is a non-aromatic carbon-based ring composed of at least three carbon atoms. Examples of cycloalkyl groups include, but are not limited to, cyclopropyl, cyclobutyl, cyclopentyl, cyclohexyl, etc. The term "heterocycloalkyl" is a cycloalkyl group as defined above where at least one of the carbon atoms of the ring is substituted with a heteroatom such as, but not limited to, nitrogen, oxygen, sulfur, or phosphorus. The cycloalkyl group and heterocycloalkyl group can be substituted or unsubstituted. The cycloalkyl group and heterocycloalkyl group can be substituted with one or more groups including, but not limited to, alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol as described herein.

The term "cycloalkenyl" as used herein is a non-aromatic carbon-based ring composed of at least three carbon atoms and containing at least one double bound, i.e., C=C. Examples of cycloalkenyl groups include, but are not limited to, cyclopropenyl, cyclobutenyl, cyclopentenyl, cyclopentadienyl, cyclohexenyl, cyclohexadienyl, and the like. The term "heterocycloalkenyl" is a type of cycloalkenyl group as defined above, and is included within the meaning of the term "cycloalkenyl," where at least one of the carbon atoms of the ring is substituted with a heteroatom such as, but not limited to, nitrogen, oxygen, sulfur, or phosphorus. The cycloalkenyl group and heterocycloalkenyl group can be substituted or unsubstituted. The cycloalkenyl group and heterocycloalkenyl group can be substituted with one or more groups including, but not limited to, alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol as described herein.

The term "cyclic group" is used herein to refer to either aryl groups, non-aryl groups (i.e., cycloalkyl, heterocycloalkyl, cycloalkenyl, and heterocycloalkenyl groups), or both. Cyclic groups have one or more ring systems that can be substituted or unsubstituted. A cyclic group can contain one or more aryl groups, one or more non-aryl groups, or one or more aryl groups and one or more non-aryl groups.

The term "aldehyde" as used herein is represented by the formula —C(O)H. Throughout this specification "C(O)" or "CO" is a short hand notation for C=O.

The terms "amine" or "amino" as used herein are represented by the formula —NZ$^1$Z$^2$, where Z$^1$ and Z$^2$ can each be substitution group as described herein, such as hydrogen, an alkyl, halogenated alkyl, alkenyl, alkynyl, aryl, heteroaryl, cycloalkyl, cycloalkenyl, heterocycloalkyl, or heterocycloalkenyl group described above.

The term "carboxylic acid" as used herein is represented by the formula —C(O)OH. A "carboxylate" or "carboxyl" group as used herein is represented by the formula —C(O)O$^-$.

The term "ester" as used herein is represented by the formula —OC(O)Z$^1$ or —C(O)OZ$^1$, where Z$^1$ can be an alkyl, halogenated alkyl, alkenyl, alkynyl, aryl, heteroaryl, cycloalkyl, cycloalkenyl, heterocycloalkyl, or heterocycloalkenyl group described above.

The term "ether" as used herein is represented by the formula Z$^1$OZ$^2$, where Z$^1$ and Z$^2$ can be, independently, an alkyl, halogenated alkyl, alkenyl, alkynyl, aryl, heteroaryl, cycloalkyl, cycloalkenyl, heterocycloalkyl, or heterocycloalkenyl group described above.

The term "ketone" as used herein is represented by the formula Z$^1$C(O)Z$^2$, where Z$^1$ and Z$^2$ can be, independently, an alkyl, halogenated alkyl, alkenyl, alkynyl, aryl, heteroaryl, cycloalkyl, cycloalkenyl, heterocycloalkyl, or heterocycloalkenyl group described above.

The term "halide" or "halogen" as used herein refers to the fluorine, chlorine, bromine, and iodine.

The term "hydroxyl" as used herein is represented by the formula —OH.

The term "nitro" as used herein is represented by the formula —NO$_2$.

The term "silyl" as used herein is represented by the formula —SiZ$^1$Z$^2$Z$^3$, where Z$^1$, Z$^2$, and Z$^3$ can be, independently, hydrogen, alkyl, halogenated alkyl, alkoxy, alkenyl, alkynyl, aryl, heteroaryl, cycloalkyl, cycloalkenyl, heterocycloalkyl, or heterocycloalkenyl group described above.

The term "sulfonyl" is used herein to refer to the sulfo-oxo group represented by the formula —S(O)$_2$Z$^1$, where Z$^1$ can be hydrogen, an alkyl, halogenated alkyl, alkenyl, alkynyl, aryl, heteroaryl, cycloalkyl, cycloalkenyl, heterocycloalkyl, or heterocycloalkenyl group described above.

The term "sulfonylamino" or "sulfonamide" as used herein is represented by the formula —S(O)$_2$NH—.

The term "thiol" as used herein is represented by the formula —SH.

The term "thio" as used herein is represented by the formula —S—.

"R$^1$," "R$^2$," "R$^3$," "R$^n$," etc., where n is some integer, as used herein can, independently, possess one or more of the groups listed above. For example, if R$^1$ is a straight chain alkyl group, one of the hydrogen atoms of the alkyl group can optionally be substituted with a hydroxyl group, an alkoxy group, an amine group, an alkyl group, a halide, and the like. Depending upon the groups that are selected, a first group can be incorporated within second group or, alternatively, the first group can be pendant (i.e., attached) to the second group. For example, with the phrase "an alkyl group comprising an amino group," the amino group can be incorporated within the backbone of the alkyl group. Alternatively, the amino group can be attached to the backbone of the alkyl group. The nature of the group(s) that is (are) selected will determine if the first group is embedded or attached to the second group.

Unless stated to the contrary, a formula with chemical bonds shown only as solid lines and not as wedges or dashed lines contemplates each possible isomer, e.g., each enantiomer, diastereomer, and meso compound, and a mixture of isomers, such as a racemic or scalemic mixture.

Reference will now be made in detail to specific aspects of the disclosed materials, compounds, compositions, articles, and methods, examples of which are illustrated in the accompanying Examples.

The examples below are intended to further illustrate certain aspects of the methods and compounds described herein, and are not intended to limit the scope of the claims.

Compounds

Marinopyrrole derivatives that can be used as antibiotic agents are described herein. The marinopyrrole derivatives disclosed herein can have the following Structure S:

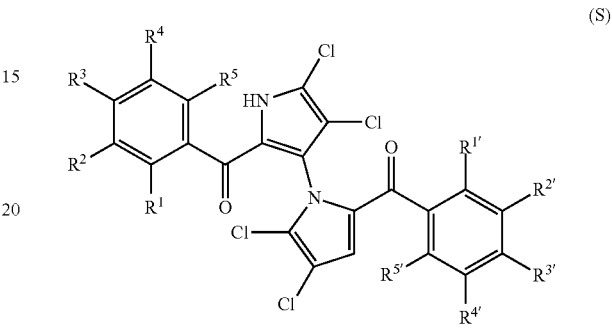

(S)

and (+), (−), and (±) isomers, and pharmaceutically acceptable salts and prodrugs thereof.

In Structure S, R$^1$, R$^2$, R$^3$, R$^4$, and R$^5$ are each independently selected from hydrogen, halogen, hydroxyl, cyano, nitro, substituted or unsubstituted amino, substituted or unsubstituted alkyl, substituted or unsubstituted heteroalkyl, substituted or unsubstituted alkenyl, substituted or unsubstituted heteroalkenyl, substituted or unsubstituted alkynyl, substituted or unsubstituted heteroalkynyl, substituted or unsubstituted aryl, substituted or unsubstituted heteroaryl, substituted or unsubstituted alkoxyl, substituted or unsubstituted aryloxyl, and substituted or unsubstituted carboxyl. Respectively, R$^{1'}$, R$^{2'}$, R$^{3'}$, R$^{4'}$, and R$^{5'}$ are the same as R$^1$, R$^2$, R$^3$, R$^4$, and R$^5$. Thus, for example, when R$^1$ is a halogen, R$^{1'}$ is the same halogen, and so forth. In compounds of Structure S, R$^1$ and R$^{1'}$ are not both OH when R$^2$, R$^{2'}$, R$^3$, R$^{3'}$, R$^4$, R$^{4'}$, R$^5$, and R$^{5'}$ are all hydrogen, i.e., the compound is not marinopyrrole A.

In Structure S, at least one of R$^1$, R$^2$, R$^3$, R$^4$, and R$^5$ is the halogen F, Cl, Br, or I, and thus the corresponding R$^{1'}$, R$^{2'}$, R$^{3'}$, R$^{4'}$, or R$^{5'}$ is the same halogen. In some examples, one or more of R$^1$, R$^2$, R$^3$, R$^4$, and R$^5$ are independently selected from hydrogen, OH, O—CH$_3$, O-alkyl, O-heteroalkyl, O-aryl, O-heteroaryl, NH$_2$, NHR$^{16}$ (where R$^{16}$ is alkyl heteroalkyl, aryl, or heteroaryl), NH-alkyl, NH-aryl, NH-heteroaryl, and halogen. In some examples, one or more of R$^1$, R$^2$, R$^3$, R$^4$, and R$^5$ are halogenated alkyl. In some examples, one of R$^1$, R$^2$, R$^3$, R$^4$, and R$^5$ is a hydroxyl. In a specific example, R$^1$ is OH and R$^3$ is CF$_3$, when R$^2$, R$^4$, and R$^5$ are hydrogen. As noted, R$^{1'}$, R$^{2'}$, R$^{3'}$, R$^{4'}$, and R$^{5'}$ are respectively the same as R$^1$, R$^2$, R$^3$, R$^4$, and R$^5$.

Optionally in Structure S, adjacent R groups, R$^1$ and R$^2$, R$^2$ and R$^3$, R$^3$ and R$^4$, or R$^4$ and R$^5$, and likewise R$^{1'}$ and R$^{2'}$, R$^{2'}$ and R$^{3'}$, R$^{3'}$ and R$^{4'}$, or R$^{4'}$ and R$^{5'}$ can be combined to form a substituted or unsubstituted aryl, substituted or unsubstituted heteroaryl, substituted or unsubstituted cycloalkyl, substituted or unsubstituted cycloalkenyl, substituted or unsubstituted cycloalkynyl, substituted or unsubstituted heterocycloalkyl, substituted or unsubstituted heterocycloalkenyl, or substituted or unsubstituted heterocycloalkynyl. For example, R$^1$ can be a substituted or unsubstituted ethylene group and R$^2$ can be a substituted or unsubstituted propylene group that combine to form a substituted or unsubstituted phenyl.

In some examples of Structure S, $R^4$ and $R^5$ as well as $R^{4'}$ and $R^{5'}$ combine to form an unsubstituted phenyl as shown in Structure S-1. In other examples of Structure S, $R^4$ and $R^3$ as well as $R^{4'}$ and $R^{3'}$ combine to form an unsubstituted phenyl as shown in Structure S-2. In still other examples of Structure S, $R^3$ and $R^2$ as well as $R^{3'}$ and $R^{22}$ combine to form an unsubstituted phenyl as shown in Structure S-3.

Structure S-1

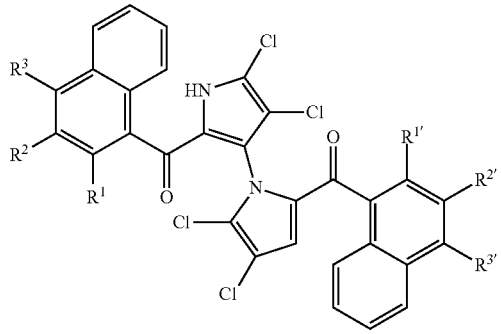

Structure S-2

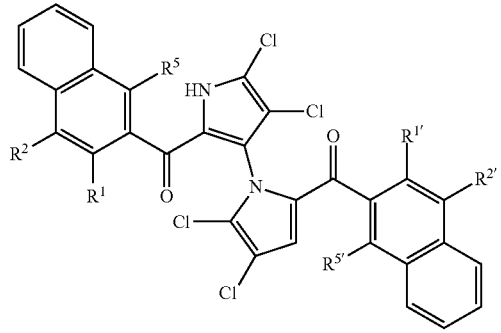

Structure S-3

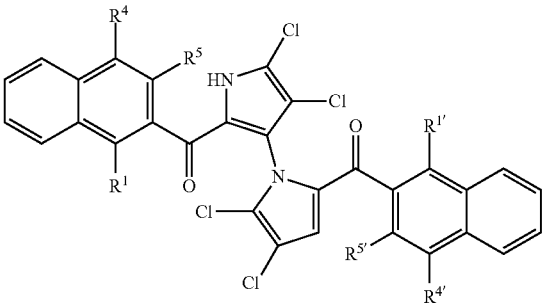

Particular examples of Structure S are shown in Chart 1

Chart 1. Marinopyrrole A and its Derivatives

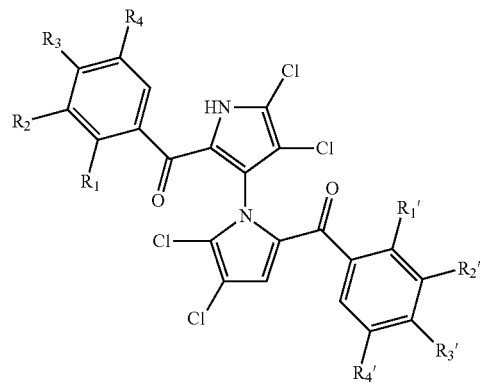

| Compd | $R_1$ | $R_2$ | $R_3$ | $R_4$ | $R_1'$ | $R_2'$ | $R_3'$ | $R_4'$ |
|---|---|---|---|---|---|---|---|---|
| 1c | OMe | H | H | H | OMe | H | H | H |
| 1d | H | H | H | H | H | H | H | H |
| 1e | H | OMe | H | H | H | OMe | H | H |
| 1f | H | H | OMe | H | H | H | OMe | H |
| 1g | F | H | H | H | F | H | H | H |
| 1h | H | F | H | H | H | F | H | H |
| 1i | H | H | F | H | H | H | F | H |
| 1j | $CF_3$ | H | H | H | $CF_3$ | H | H | H |
| 1k | H | H | $CF_3$ | H | H | H | $CF_3$ | H |
| 1m | OH | H | OMe | Cl | OH | H | OMe | Cl |
| 1n | OMe | H | OMe | Cl | OMe | H | OMe | Cl |
| I | OH | H | H | Cl | OH | H | H | Cl |
| II | OH | H | Cl | H | OH | H | Cl | H |
| III | OH | Cl | H | H | OH | Cl | H | H |
| IV | OMe | H | H | Cl | OMe | H | H | Cl |
| V | OMe | H | Cl | H | OMe | H | Cl | H |
| VI | OMe | Cl | H | H | OMe | Cl | H | H |
| VII | OMe | H | H | F | OMe | H | H | F |
| VIII | OMe | H | H | F | OMe | H | H | F |
| IX | OMe | F | H | H | OMe | F | H | H |
| X | OH | H | H | F | OH | H | H | F |
| XI | OH | H | F | H | OH | H | F | H |
| XII | OH | F | H | H | OH | F | H | H |
| XIII | OMe | H | OMe | Cl | OMe | H | OMe | Cl |
| XIV | OH | Cl | Together Phenyl | | OH | Cl | Together Phenyl | |
| XV | OH | Together Phenyl | | Cl | OH | Together Phenyl | | Cl |
| XVI | OMe | Cl | Together Phenyl | | OMe | Cl | Together Phenyl | |
| XVII | OMe | Together Phenyl | | Cl | OMe | Together Phenyl | | Cl |
| CCW14 | OH | H | Me | Cl | OH | H | Me | Cl |
| CCW31 | OH | H | CO2Me | H | OH | H | CO2Me | Cl |

In certain examples, marinopyrrole derivatives can have the following Structure S-4.

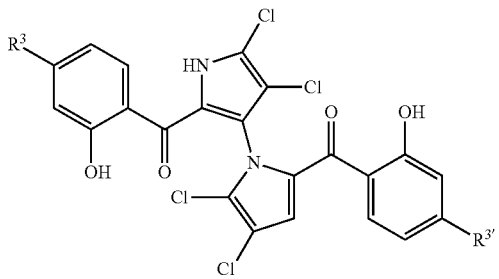

Structure S-4 and (+), (−), and (±) isomers, and pharmaceutically acceptable salts and prodrugs thereof, where in $R^3$ and $R^{3'}$ are selected from hydrogen, halogen, hydroxyl, cyano, nitro, substituted or unsubstituted amino, substituted or unsubstituted alkyl, substituted or unsubstituted heteroalkyl, substituted or unsubstituted alkenyl, substituted or unsubstituted heteroalkenyl, substituted or unsubstituted alkynyl, substituted or unsubstituted heteroalkynyl, substituted or unsubstituted aryl, substituted or unsubstituted heteroaryl, substituted or unsubstituted alkoxyl, substituted or unsubstituted aryloxyl, and substituted or unsubstituted carboxyl.

In a specific example, the marinopyrrole derivative has the Structure 41.

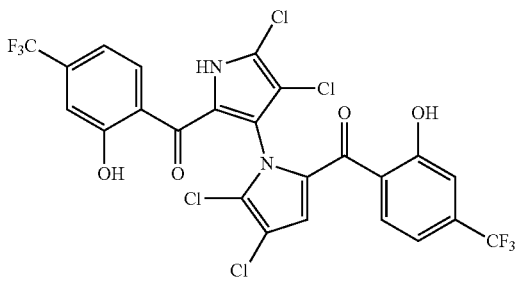 [SMILES: O=C(c1ccc(C(F)(F)F)cc1O)c1[nH]c(Cl)c(Cl)c1-n1c(C(=O)c2ccc(C(F)(F)F)cc2O)cc(Cl)c1Cl]

Structure 41

Pharmaceutical Compositions

The compounds described herein or derivatives thereof can be provided in a pharmaceutical composition. Depending on the intended mode of administration, the pharmaceutical composition can be in the form of solid, semi-solid or liquid dosage forms, such as, for example, tablets, suppositories, pills, capsules, powders, liquids, or suspensions, preferably in unit dosage form suitable for single administration of a precise dosage. The compositions will include a therapeutically effective amount of the compound described herein or derivatives thereof in combination with a pharmaceutically acceptable carrier and, in addition, can include other medicinal agents, pharmaceutical agents, carriers, or diluents. By pharmaceutically acceptable is meant a material that is not biologically or otherwise undesirable, which can be administered to an individual along with the selected compound without causing unacceptable biological effects or interacting in a deleterious manner with the other components of the pharmaceutical composition in which it is contained.

As used herein, the term carrier encompasses any excipient, diluent, filler, salt, buffer, stabilizer, solubilizer, lipid, stabilizer, or other material well known in the art for use in pharmaceutical formulations. The choice of a carrier for use in a composition will depend upon the intended route of administration for the composition. The preparation of pharmaceutically acceptable carriers and formulations containing these materials is described in, e.g., Remington's Pharmaceutical Sciences, 21st Edition, ed. University of the Sciences in Philadelphia, Lippincott, Williams & Wilkins, Philadelphia Pa., 2005. Examples of physiologically acceptable carriers include buffers such as phosphate buffers, citrate buffer, and buffers with other organic acids; antioxidants including ascorbic acid; low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN™ (ICI, Inc.; Bridgewater, N.J.), polyethylene glycol (PEG), and PLURONICS™ (BASF; Florham Park, N.J.).

Compositions containing the compound described herein or derivatives thereof suitable for parenteral injection can comprise physiologically acceptable sterile aqueous or non-aqueous solutions, dispersions, suspensions or emulsions, and sterile powders for reconstitution into sterile injectable solutions or dispersions. Examples of suitable aqueous and nonaqueous carriers, diluents, solvents or vehicles include water, ethanol, polyols (propyleneglycol, polyethyleneglycol, glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions and by the use of surfactants.

These compositions can also contain adjuvants such as preserving, wetting, emulsifying, and dispensing agents. Prevention of the action of microorganisms can be promoted by various antibacterial and antifungal agents, for example, parabens, chlorobutanol, phenol, sorbic acid, and the like. Isotonic agents, for example, sugars, sodium chloride, and the like can also be included. Prolonged absorption of the injectable pharmaceutical form can be brought about by the use of agents delaying absorption, for example, aluminum monostearate and gelatin.

Solid dosage forms for oral administration of the compounds described herein or derivatives thereof include capsules, tablets, pills, powders, and granules. In such solid dosage forms, the compounds described herein or derivatives thereof is admixed with at least one inert customary excipient (or carrier) such as sodium citrate or dicalcium phosphate or (a) fillers or extenders, as for example, starches, lactose, sucrose, glucose, mannitol, and silicic acid, (b) binders, as for example, carboxymethylcellulose, alignates, gelatin, polyvinylpyrrolidone, sucrose, and acacia, (c) humectants, as for example, glycerol, (d) disintegrating agents, as for example, agar-agar, calcium carbonate, potato or tapioca starch, alginic acid, certain complex silicates, and sodium carbonate, (e) solution retarders, as for example, paraffin, (f) absorption accelerators, as for example, quaternary ammonium compounds, (g) wetting agents, as for example, cetyl alcohol, and glycerol monostearate, (h) adsorbents, as for example, kaolin and bentonite, and (i)

lubricants, as for example, talc, calcium stearate, magnesium stearate, solid polyethylene glycols, sodium lauryl sulfate, or mixtures thereof. In the case of capsules, tablets, and pills, the dosage forms can also comprise buffering agents.

Solid compositions of a similar type can also be employed as fillers in soft and hard-filled gelatin capsules using such excipients as lactose or milk sugar as well as high molecular weight polyethyleneglycols, and the like.

Solid dosage forms such as tablets, dragees, capsules, pills, and granules can be prepared with coatings and shells, such as enteric coatings and others known in the art. They can contain opacifying agents and can also be of such composition that they release the active compound or compounds in a certain part of the intestinal tract in a delayed manner. Examples of embedding compositions that can be used are polymeric substances and waxes. The active compounds can also be in micro-encapsulated form, if appropriate, with one or more of the above-mentioned excipients.

Liquid dosage forms for oral administration of the compounds described herein or derivatives thereof include pharmaceutically acceptable emulsions, solutions, suspensions, syrups, and elixirs. In addition to the active compounds, the liquid dosage forms can contain inert diluents commonly used in the art, such as water or other solvents, solubilizing agents, and emulsifiers, as for example, ethyl alcohol, isopropyl alcohol, ethyl carbonate, ethyl acetate, benzyl alcohol, benzyl benzoate, propyleneglycol, 1,3-butyleneglycol, dimethylformamide, oils, in particular, cottonseed oil, groundnut oil, corn germ oil, olive oil, castor oil, sesame oil, glycerol, tetrahydrofurfuryl alcohol, polyethyleneglycols, and fatty acid esters of sorbitan, or mixtures of these substances, and the like.

Besides such inert diluents, the composition can also include additional agents, such as wetting, emulsifying, suspending, sweetening, flavoring, or perfuming agents.

Suspensions, in addition to the active compounds, can contain additional agents, as for example, ethoxylated isostearyl alcohols, polyoxyethylene sorbitol and sorbitan esters, microcrystalline cellulose, aluminum metahydroxide, bentonite, agar-agar and tragacanth, or mixtures of these substances, and the like.

Compositions of the compounds described herein or derivatives thereof for rectal administrations are optionally suppositories, which can be prepared by mixing the compounds with suitable non-irritating excipients or carriers such as cocoa butter, polyethyleneglycol or a suppository wax, which are solid at ordinary temperatures but liquid at body temperature and therefore, melt in the rectum or vaginal cavity and release the active component.

Dosage forms for topical administration of the compounds described herein or derivatives thereof include ointments, powders, sprays, and inhalants. The compounds described herein or derivatives thereof are admixed under sterile conditions with a physiologically acceptable carrier and any preservatives, buffers, or propellants as can be required. Ophthalmic formulations, ointments, powders, and solutions are also contemplated as being within the scope of the compositions.

The compositions can include one or more of the compounds described herein and a pharmaceutically acceptable carrier. As used herein, the term pharmaceutically acceptable salt refers to those salts of the compound described herein or derivatives thereof that are, within the scope of sound medical judgment, suitable for use in contact with the tissues of subjects without undue toxicity, irritation, allergic response, and the like, commensurate with a reasonable benefit/risk ratio, and effective for their intended use, as well as the zwitterionic forms, where possible, of the compounds described herein. The term salts refers to the relatively non-toxic, inorganic and organic acid addition salts of the compounds described herein. These salts can be prepared in situ during the isolation and purification of the compounds or by separately reacting the purified compound in its free base form with a suitable organic or inorganic acid and isolating the salt thus formed. Representative salts include the hydrobromide, hydrochloride, sulfate, bisulfate, nitrate, acetate, oxalate, valerate, oleate, palmitate, stearate, laurate, borate, benzoate, lactate, phosphate, tosylate, citrate, maleate, fumarate, succinate, tartrate, naphthylate mesylate, glucoheptonate, lactobionate, methane sulphonate, and laurylsulphonate salts, and the like. These can include cations based on the alkali and alkaline earth metals, such as sodium, lithium, potassium, calcium, magnesium, and the like, as well as non-toxic ammonium, quaternary ammonium, and amine cations including, but not limited to ammonium, tetramethylammonium, tetraethylammonium, methylamine, dimethylamine, trimethylamine, triethylamine, ethylamine, and the like. (See S. M. Barge et al., *J. Pharm. Sci.* (1977) 66, 1, which is incorporated herein by reference in its entirety, at least, for compositions taught herein.)

Administration of the compounds and compositions described herein or pharmaceutically acceptable salts thereof to a subject can be carried out using therapeutically effective amounts of the compounds and compositions described herein or pharmaceutically acceptable salts thereof as described herein for periods of time effective to treat a disorder.

The effective amount of the compounds and compositions described herein or pharmaceutically acceptable salts thereof as described herein can be determined by one of ordinary skill in the art and includes exemplary dosage amounts for a mammal of from about 0.5 to about 200 mg/kg of body weight of active compound per day, which can be administered in a single dose or in the form of individual divided doses, such as from 1 to 4 times per day. Alternatively, the dosage amount can be from about 0.5 to about 150 mg/kg of body weight of active compound per day, about 0.5 to 100 mg/kg of body weight of active compound per day, about 0.5 to about 75 mg/kg of body weight of active compound per day, about 0.5 to about 50 mg/kg of body weight of active compound per day, about 0.5 to about 25 mg/kg of body weight of active compound per day, about 1 to about 20 mg/kg of body weight of active compound per day, about 1 to about 10 mg/kg of body weight of active compound per day, about 20 mg/kg of body weight of active compound per day, about 10 mg/kg of body weight of active compound per day, or about 5 mg/kg of body weight of active compound per day. The expression effective amount, when used to describe an amount of compound in a method, refers to the amount of a compound that achieves the desired pharmacological effect or other effect, for example an amount that results in bacterial enzyme inhibition.

Those of skill in the art will understand that the specific dose level and frequency of dosage for any particular subject can be varied and will depend upon a variety of factors, including the activity of the specific compound employed, the metabolic stability and length of action of that compound, the species, age, body weight, general health, sex and diet of the subject, the mode and time of administration, rate of excretion, drug combination, and severity of the particular condition.

Methods of Making the Compounds

The compounds described herein can be prepared in a variety of ways known to one skilled in the art of organic synthesis or variations thereon as appreciated by those skilled in the art. The compounds described herein can be prepared from readily available starting materials. Optimum reaction conditions can vary with the particular reactants or solvents used, but such conditions can be determined by one skilled in the art.

Variations on Structure S include the addition, subtraction, or movement of the various constituents as described for each compound. Similarly, when one or more chiral centers are present in a molecule, the chirality of the molecule can be changed. Additionally, compound synthesis can involve the protection and deprotection of various chemical groups. The use of protection and deprotection, and the selection of appropriate protecting groups can be determined by one skilled in the art. The chemistry of protecting groups can be found, for example, in Wuts and Greene, Protective Groups in Organic Synthesis, 4th Ed., Wiley & Sons, 2006, which is incorporated herein by reference in its entirety.

The starting materials and reagents used in preparing the disclosed compounds and compositions are either available from commercial suppliers such as Aldrich Chemical Co., (Milwaukee, Wis.), Acros Organics (Morris Plains, N.J.), Fisher Scientific (Pittsburgh, Pa.), Sigma (St. Louis, Mo.), Pfizer (New York, N.Y.), GlaxoSmithKline (Raleigh, N.C.), Merck (Whitehouse Station, N.J.), Johnson & Johnson (New Brunswick, N.J.), Aventis (Bridgewater, N.J.), AstraZeneca (Wilmington, Del.), Novartis (Basel, Switzerland), Wyeth (Madison, N.J.), Bristol-Myers-Squibb (New York, N.Y.), Roche (Basel, Switzerland), Lilly (Indianapolis, Ind.), Abbott (Abbott Park, Ill.), Schering Plough (Kenilworth, N.J.), or Boehringer Ingelheim (Ingelheim, Germany), or are prepared by methods known to those skilled in the art following procedures set forth in references such as Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991); March's Advanced Organic Chemistry, (John Wiley and Sons, 4th Edition); and Larock's Comprehensive Organic Transformations (VCH Publishers Inc., 1989). Other materials, such as the pharmaceutical carriers disclosed herein can be obtained from commercial sources.

Reactions to produce the compounds described herein can be carried out in solvents, which can be selected by one of skill in the art of organic synthesis. Solvents can be substantially nonreactive with the starting materials (reactants), the intermediates, or products under the conditions at which the reactions are carried out, i.e., temperature and pressure. Reactions can be carried out in one solvent or a mixture of more than one solvent. Product or intermediate formation can be monitored according to any suitable method known in the art. For example, product formation can be monitored by spectroscopic means, such as nuclear magnetic resonance spectroscopy (e.g., $^1H$ or $^{13}C$) infrared spectroscopy, spectrophotometry (e.g., UV-visible), or mass spectrometry, or by chromatography such as high performance liquid chromatography (HPLC) or thin layer chromatography.

The first total synthesis of (±)-marinopyrrole A (1) and a dozen "symmetrical" derivatives were recent disclosed, which bear the same substituents with the same substitution patterns on both ring A and B attached to the carbonyl groups as shown in 1 (Scheme 1) (Cheng et al., "Total synthesis of (±)-marinopyrrole a and its library as potential antibiotic and anticancer agents," *J Comb Chem* 12:541-547, 2010, which is incorporated by reference herein for its teachings of marinopyrrole derivatives and synthesis).

Scheme 1. Synthesis of Marinopyrrole A

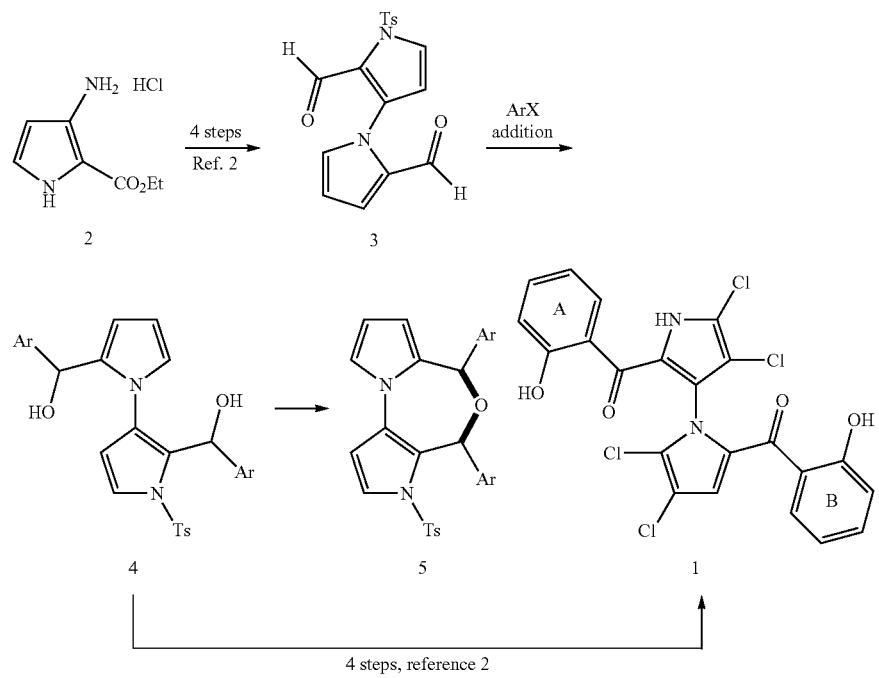

The total synthesis required nine-steps to access (±)-marinopyrrole A, in which a limiting step was the formation of oxazepine byproduct. This synthesis was modified to circumvent some chemistry issues (Pan et al., "Optimization of synthetic method of marinopyrrole A derivatives," *Chem J Chinese Universities* 33:1476-1480, 2012, which is incorporated by reference herein for its teachings of marinopyrrole derivatives and synthesis).

As shown in Scheme 1, the formation of byproduct oxazepine 5 after Grignard addition to aldehyde 3 followed by work-up under a weak acid condition (AcOH) can not be avoided due to reactive diol intermediate 4. Oxazepine 5 can be readily formed even on silica gel with attempted purification by column chromatography. Although this issue was evaded by direct oxidation of the crude diol 4 to ketone, the reproducibility suffered and the yields varied from batch to batch. The key to solve such chemistry issues was sequential introduction of ring A and B, for instance, via monoprotection of aldehyde 3 as reported in Pan et al. In this paper, the alternative approaches to accomplishing the sequential introduction of ring A and B are reported.

As shown in Scheme 2, selective oxidation of diol 6 was achieved by IBX in DMSO in 72% yield. Protection of 7 with TBDMS afforded intermediate 8 in 70% yield. Addition of 9 to aldehyde 8 in 90% yield followed by oxidation of the resulting alcohol 10 by IBX in DMSO afforded ketone 11 in 82% yield. The second aldehyde 13 was obtained by removal of the silyl protecting group in 11 by TBAF in 95% yield followed by oxidation by IBX in DMSO in 96% yield. Addition of 9 to 13 followed by oxidation by IBX in DMSO afforded diketone 15 in 72% yield for two steps. It is worthwhile to note that this new synthetic strategy is versatile. The strategy has paved the avenue to access not only the "symmetrical" marinopyrroles but also "asymmetrical" congeners when two different Grignard or organic lithium reagents are used. Deprotection of diketone 15 by hydrogenolysis furnished 16. Removal of tosyl protecting group by KOH generated 17 which was then converted to 18 by tetrachlorination with NCS. The final symmetrical marinopyrrole derivative 19 was obtained after demethylation using $BBr_3$/DCM.

Scheme 2. General Route for the Synthesis of Marinopyrrole Derivatives 18 and 19

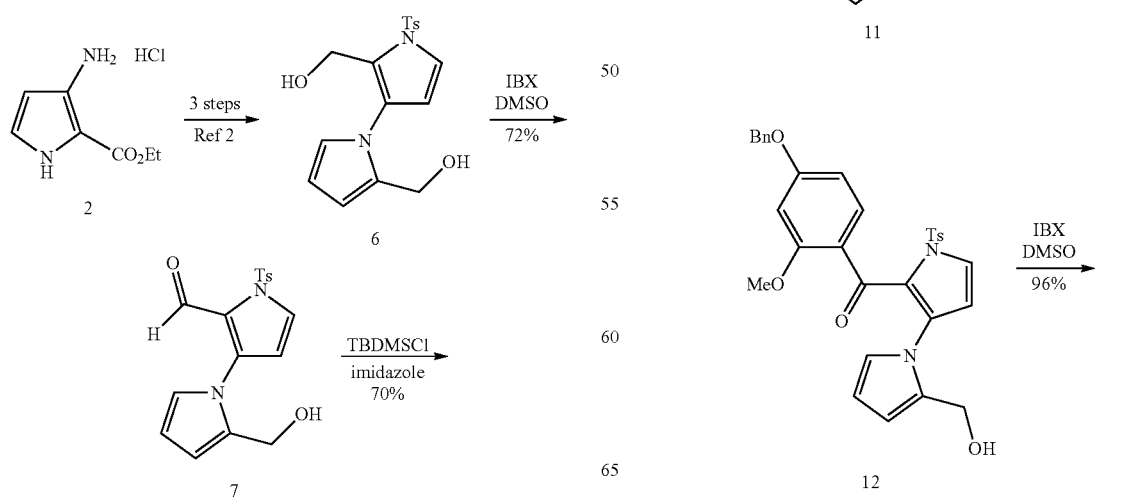

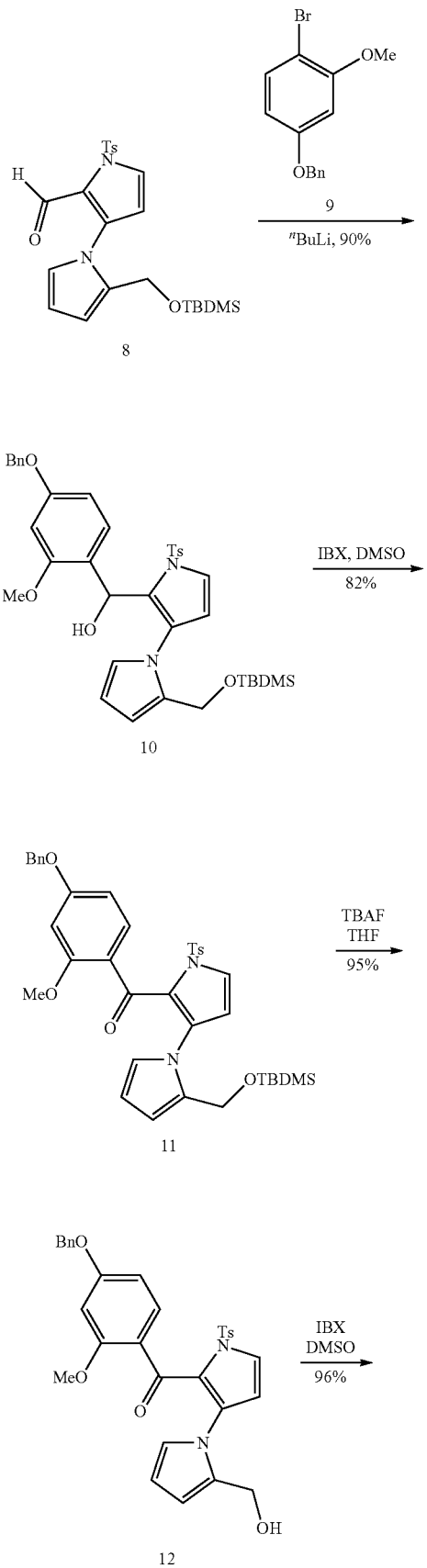

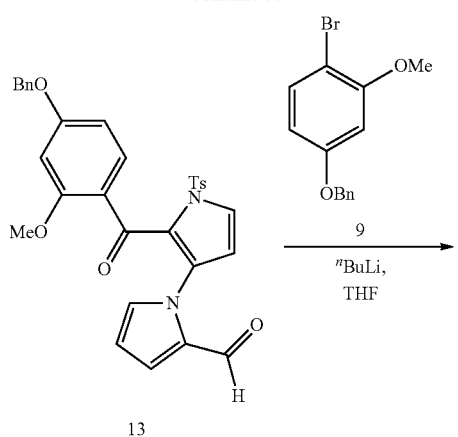
13
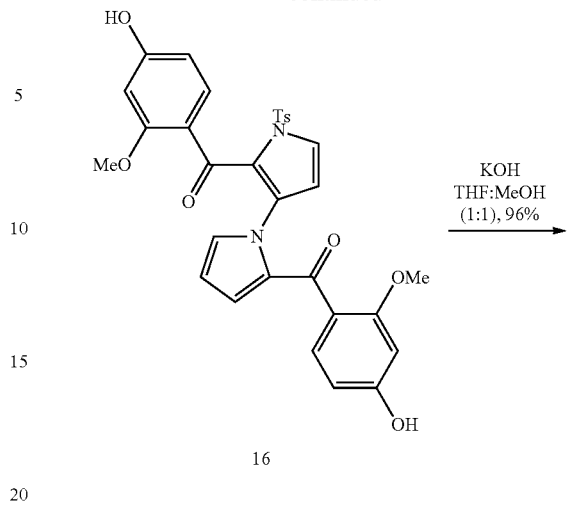
16
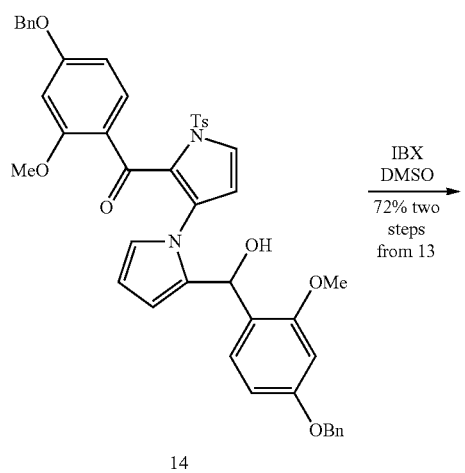
14
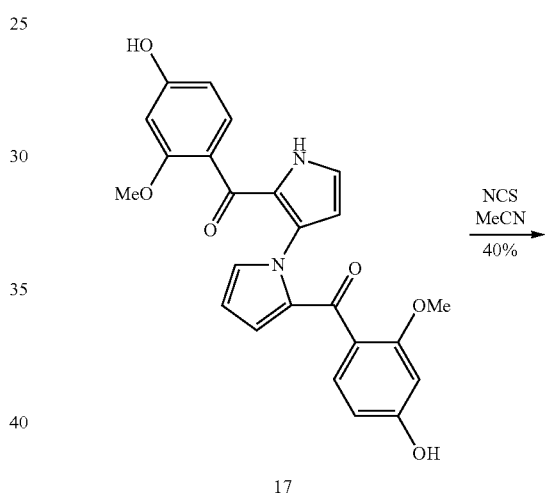
17
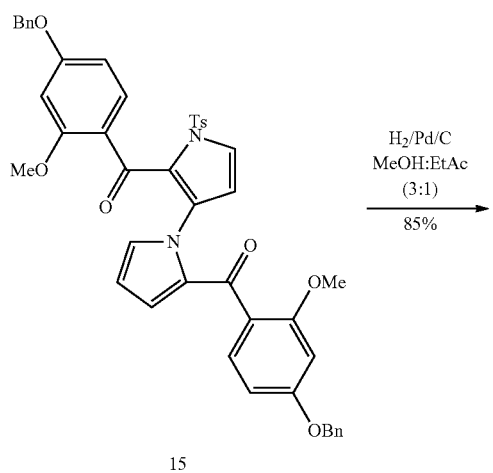
15
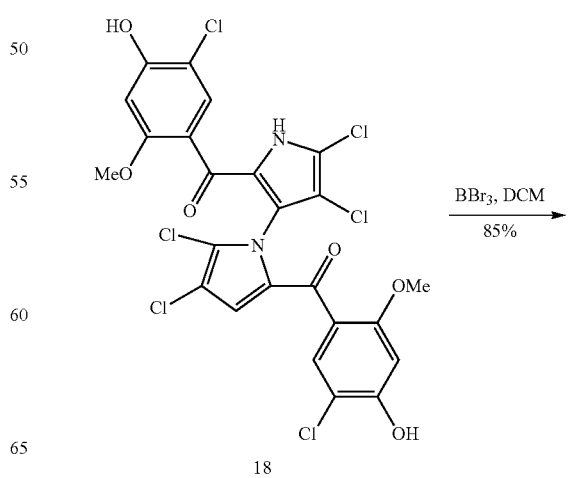
18

-continued

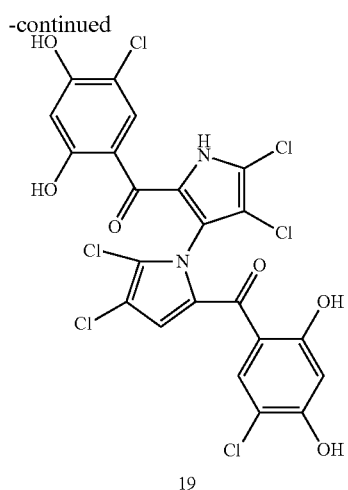

19

Scheme 3 shows the synthetic route to access the marinopyrrole derivatives 24-32. With intermediate 16 as a starting material, two phenolic hydroxyl groups were activated by trifluoromethanesufonic anhydride in the presence of DIEA in anhydrous acetonitrile. Tetrachlorination of 20 with NCS in DMF furnished 21 in 35% yield. Demethylation of 21 with BBr₃ followed by removal of tosyl protecting group afforded a common intermediate 23. Compound 24 was obtained after removal of Tf with KF in 75% yield. Compounds 25-27 were obtained by palladium mediated nucleophilic substitution of the triflate 23 with ethyl 2-mecaptoacetate, phenylmethanethiol and (4-methoxyphenyl)methanethiol, respectively in 61%-96% yields. Compounds 25-26 were oxidized to the corresponding sulfones 28-30 using m-chloroperbenzoic acid (m-CPBA) in 65%-75% yields. The carboxylic acids 31 and 32 were obtained by saponification of the corresponding esters 25 and 28 using LiOH in 85% and 95% yields, respectively.

Scheme 3. Synthesis of Marinopyrrole Derivatives 24-32

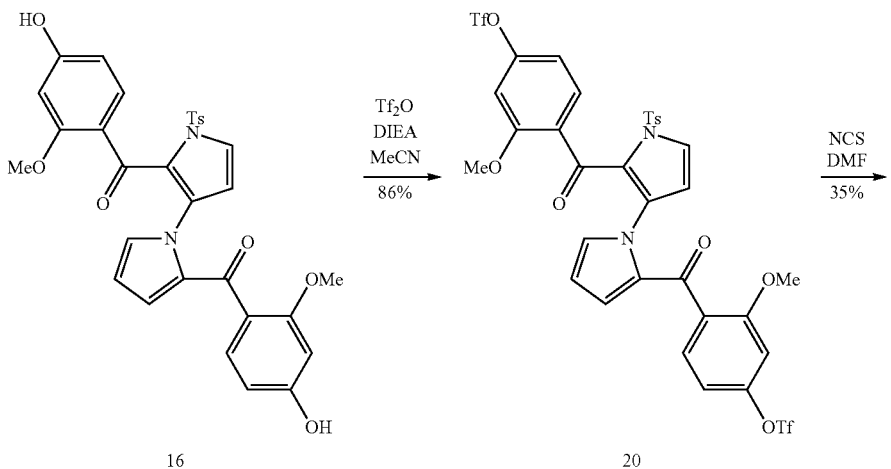

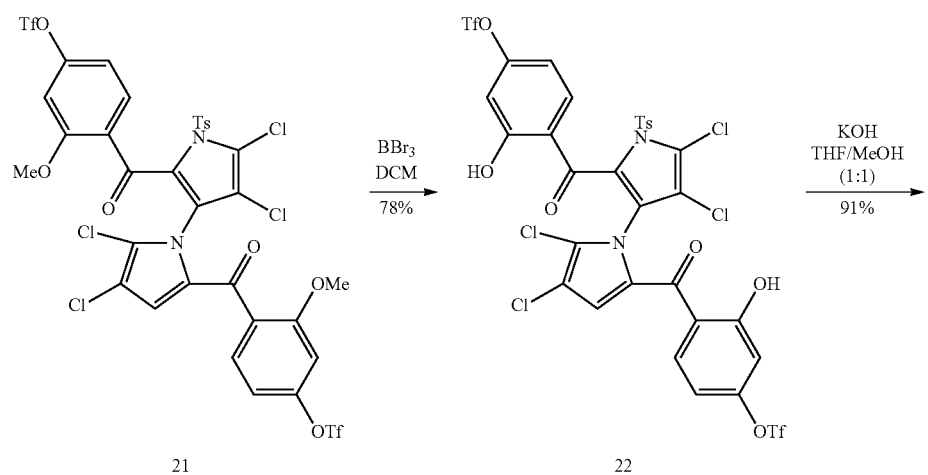

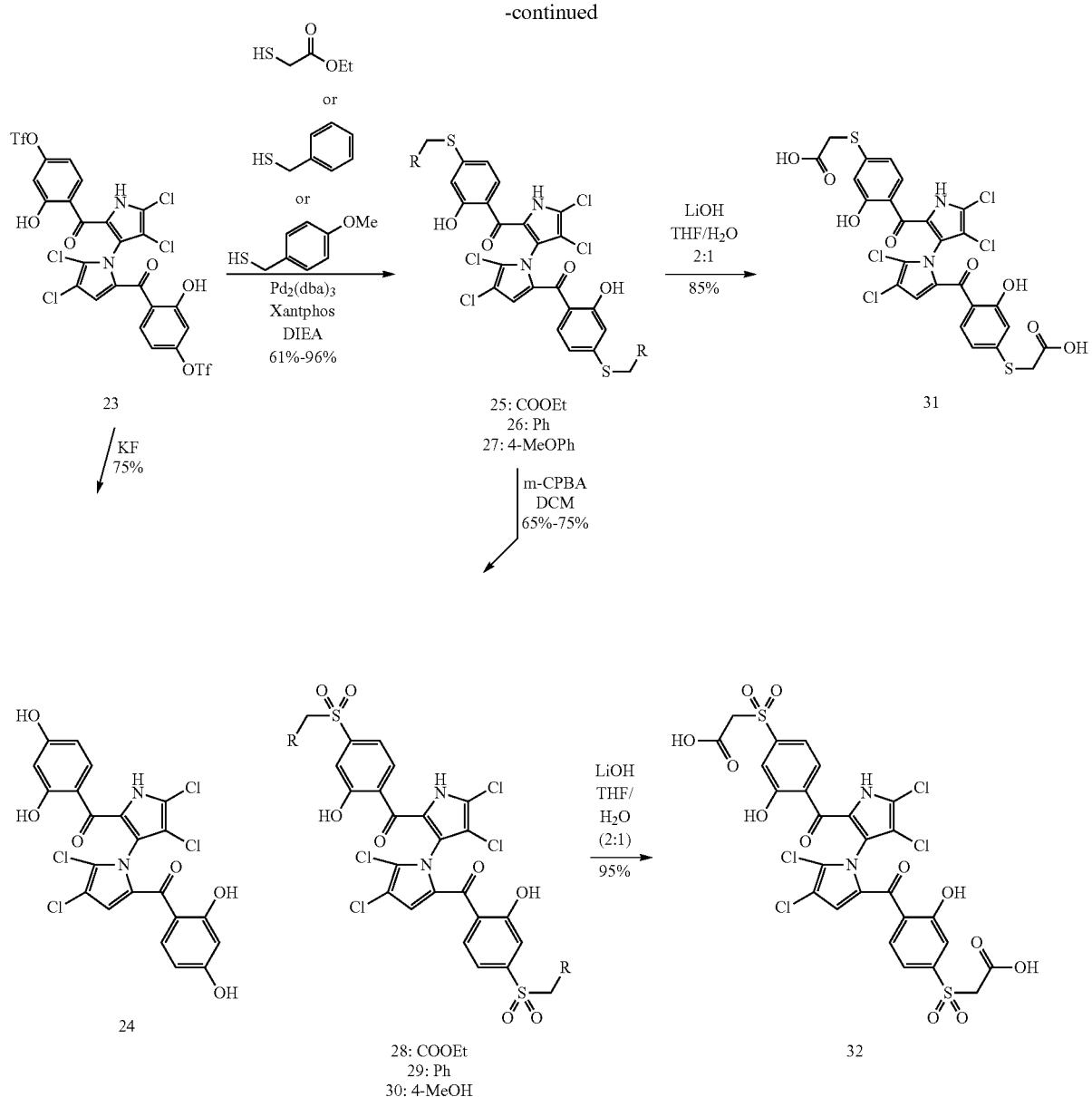

A nine step sequence to access symmetrical marinopyrrole derivative 41 is shown in Scheme 4. Similar to the synthetic route towards compound 19, (2-methoxy-4-(trifluoromethyl)phenyl)lithium was added to aldehyde 8 followed by oxidation of 33 by IBX in DMSO to afford 34. Second addition of (2-methoxy-4-(trifluoromethyl)phenyl)lithium to aldehyde 36, generated by removal of TBDMS in 34 with TBAF followed by IBX oxidation of 35, furnished 37. Diketone 38 was obtained after oxidation of 37 with IBX in DMSO in 84% yield. Removal of tosyl group in 38 afforded 39 which was then subjected to demethylation using BBr$_3$ in DCM in 82% yield. The final compound 41 was obtained after tetrachlorination of 40 with NCS in MeCN.

Scheme 4. Synthesis of Marinopyrrole Derivative 41

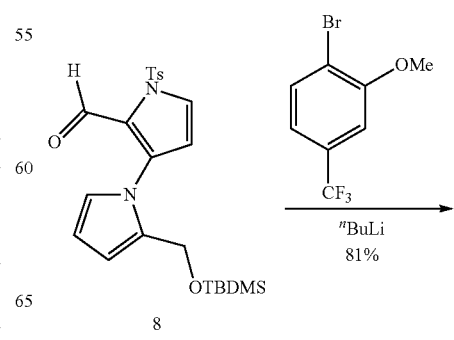

25
-continued
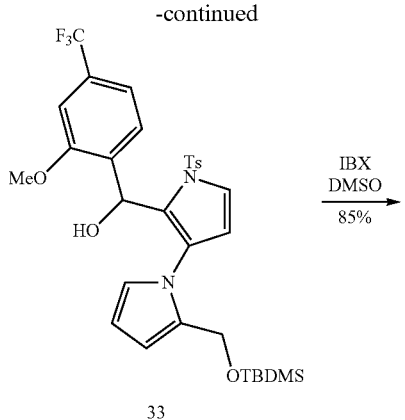
33
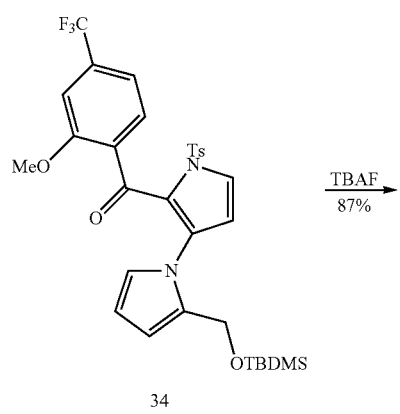
34
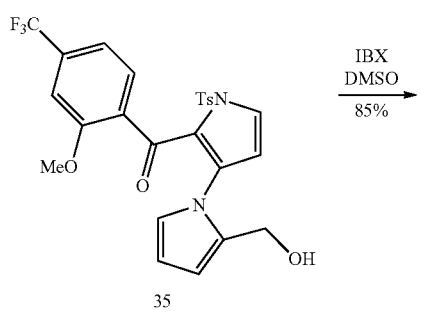
35
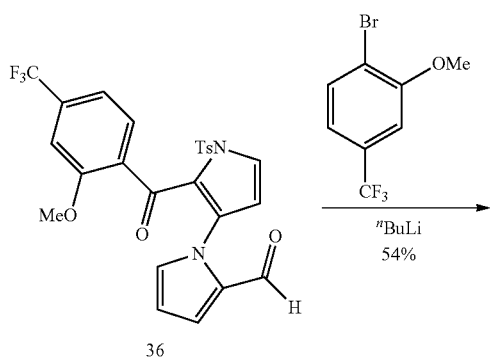
36
26
-continued
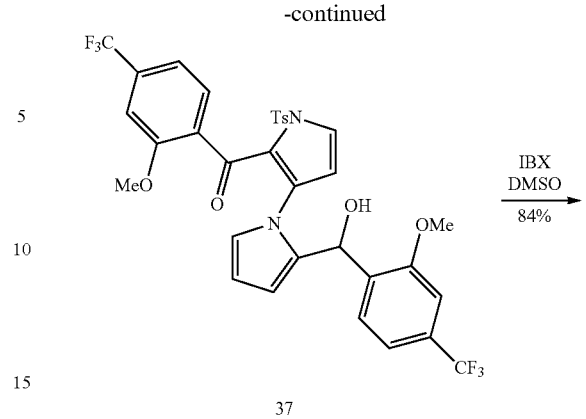
37
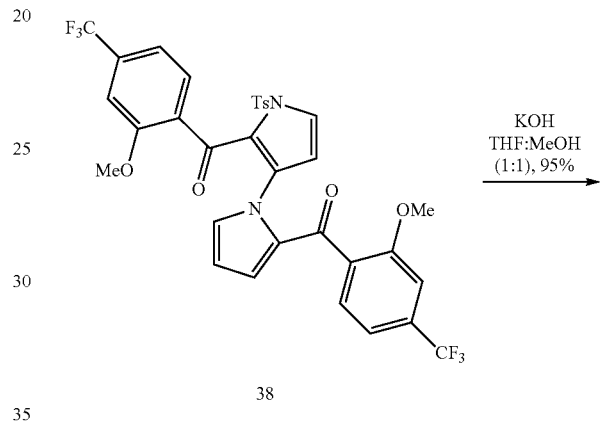
38
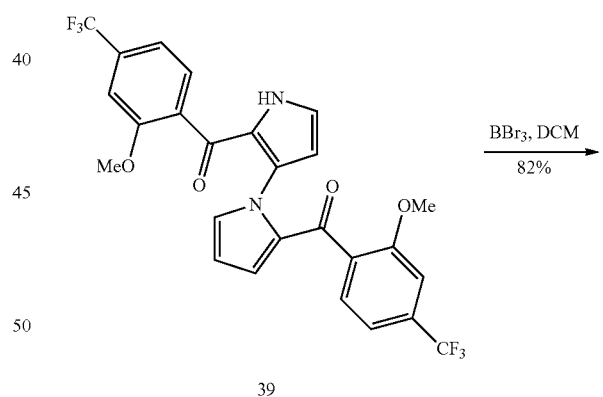
39
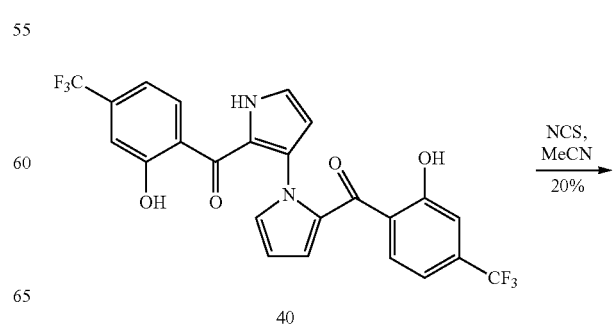
40

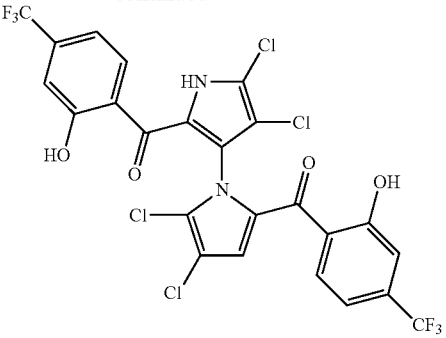

41

Activity Assays

The activity of the compounds provided herein as antibacterial agents can be measured in standard assays, e.g., HPLC assays. The compounds can also be evaluated for antibacterial activity using the Mueller Hinton (MH) broth antibacterial assay as specified by the Clinical and Laboratory Standards Institute MIC broth microdilution protocol (see Methods for Dilution Antimicrobial Susceptibility Tests for Bacteria That Grow Aerobically; Approved Standard, In *The Clinical and Laboratory Standards Institute (CLSI, formerly NCCLS)*, 7th ed., January 2006, 26 (2), M7-A7; see also Performance Standards for Antimicrobial Susceptibility Testing; Eighteenth Informational Supplement, In *The Clinical and Laboratory Standards Institute (CLSI, formerly NCCLS)*, January 2008, 28 (1), M100-S18.

The activities of the compounds as determined using the assays described herein can be reported in terms of $IC_{50}$ and/or MIC 100. As used herein, $IC_{50}$ refers to an amount, concentration or dosage of a particular test compound that achieves a 50% inhibition of a maximal response in an assay that measures such response. MIC 100 is used to measure the growth inhibition of cells and refers to a 100% inhibition of cell growth.

In certain aspects, the disclosed compounds and compositions need not actually be synthesized, but instead can be used as targets for any molecular modeling technique to predict and characterize interactions with bacterial enzymes. This is achieved through structural information and computer modeling. Computer modeling technology allows visualization of the three-dimensional atomic structure of a selected molecule and the rational design of new compounds that will interact with a bacterial enzyme. The three-dimensional construct of the enzyme typically depends on data from x-ray crystallographic analyses or NMR imaging of the selected molecule. The molecular dynamics require force field data (e.g., Merck Molecular Force Field). The computer graphics systems enable prediction of how a new compound will link to the enzyme and allow experimental manipulation of the structures of the compound to perfect binding specificity. Prediction of what the interactions will be when small changes are made in one or both requires molecular mechanics software and computationally intensive computers, usually coupled with user-friendly, menu-driven interfaces between the molecular design program and the user.

Examples of molecular modeling systems are the CHARMm and QUANTA programs, Polygen Corporation, Waltham, Mass. CHARMm performs the energy minimization and molecular dynamics functions. QUANTA performs the construction, graphic modeling and analysis of molecular structure. QUANTA allows interactive construction, modification, visualization, and analysis of the behavior of molecules with each other. Upon identification of compounds that interact in a desired way with the bacterial enzyme in silico, actual compounds can be synthesized and assayed as disclosed herein.

Methods of Use

Provided herein are methods to treat, prevent, or limit microbial infections in a subject. The methods include administering to a subject an effective amount of one or more of the compounds or compositions described herein, or a pharmaceutically acceptable salt thereof. The compounds and compositions described herein or pharmaceutically acceptable salts thereof are useful for treating microbial infections and cancer in humans, e.g., pediatric and geriatric populations, and in animals, e.g., veterinary applications. Microbial infections include, for example, bacterial and fungal infections. Bacterial infections include infections caused by bacilli, cocci, spirochaetes, and vibrio bacteria. In some examples, the microbial infection is a bacterial infection (e.g., a Gram positive bacterial infection). In some examples, the bacterial infection is *Staphylococcus* infection, such as a *Staphylococcus aureus*. The compounds and compositions described herein are useful in treating a variety of *Staphylococcus aureus* infections, including drug-resistant *Staphylococcus aureus* infections and biofilm-associated *Staphylococcus aureus* infections. In some embodiments, the *Staphylococcus aureus* infection is methocillin-resistant *S. aureus* (MRSA). For example, the MRSA can be hospital-associated MRSA or community associated MRSA.

The methods of treatment or prevention described herein can further include treatment with one or more additional agents (e.g., an antibacterial agent). The one or more additional agents and the compounds and compositions or pharmaceutically acceptable salts thereof as described herein can be administered in any order, including simultaneous administration, as well as temporally spaced order of up to several days apart. The methods can also include more than a single administration of the one or more additional agents and/or the compounds and compositions or pharmaceutically acceptable salts thereof as described herein. The administration of the one or more additional agents and the compounds and compositions or pharmaceutically acceptable salts thereof as described herein can be by the same or different routes. When treating with one or more additional agents, the compounds and compositions or pharmaceutically acceptable salts thereof as described herein can be combined into a pharmaceutical composition that includes the one or more additional agents. For example, the compounds or compositions or pharmaceutically acceptable salts thereof as described herein can be combined into a pharmaceutical composition with an additional antibacterial agent, such as acedapsone; acetosulfone sodium; alamecin; alexidine; amdinocillin; amdinocillin pivoxil; amicycline; amifloxacin; amifloxacin mesylate; amikacin; amikacin sulfate; aminosalicylic acid; aminosalicylate sodium; amoxicillin; amphomycin; ampicillin; ampicillin sodium; apalcillin sodium; apramycin; aspartocin; astromicin sulfate; avilamycin; avoparcin; azithromycin; azlocillin; azlocillin sodium; bacampicillin hydrochloride; bacitracin; bacitracin methylene disalicylate; bacitracin zinc; bambermycins; benzoylpas calcium; berythromycin; betamicin sulfate; biapenem; biniramycin; biphenamine hydrochloride; bispyrithione magsulfex; butikacin; butirosin sulfate; capreomycin sulfate; carbadox; carbenicillin disodium; carbenicillin indanyl sodium; carbenicillin phenyl sodium; carbenicillin potassium; carumonam sodium; cefaclor; cefadroxil; cefamandole; cefamandole nafate; cefamandole sodium; cefaparole; cefatrizine; cefazaflur sodium; cefazolin; cefazolin sodium; cefbuperazone; cefdinir; cefepime; cefepime hydrochloride; cefetecol; cefixime; cefmenoxime hydrochloride; cefmetazole; cefmetazole sodium; cefonicid monosodium; cefonicid sodium; cefoperazone sodium; ceforanide; cefotaxime sodium; cefotetan; cefotetan disodium; cefotiam hydrochloride; cefoxitin; cefoxitin sodium; cefpimizole; cefpimizole sodium; cefpiramide; cefpiramide sodium; cefpirome sulfate; cefpodoxime proxetil; cefprozil; cefroxadine; cefsulodin sodium; ceftazidime; ceftibuten; ceftizoxime sodium; ceftriaxone sodium; cefuroxime; cefuroxime axetil; cefuroxime pivoxetil; cefuroxime sodium; cephacetrile sodium; cephalexin; cephalexin hydrochloride; cephaloglycin; cephaloridine; cephalothin sodium; cephapirin sodium; cephradine; cetocycline hydrochloride; cetophenicol; chloramphenicol; chloramphenicol palmitate; chloramphenicol pantothenate complex; chloramphenicol sodium succinate; chlorhexidine phosphanilate; chloroxylenol; chlortetracycline bisulfate; chlortetracycline hydrochloride; cinoxacin; ciprofloxacin; ciprofloxacin hydrochloride; cirolemycin; clarithromycin; clinafloxacin hydrochloride; clindamycin; clindamycin hydrochloride; clindamycin palmitate hydrochloride; clindamycin phosphate; clofazimine; cloxacillin benzathine; cloxacillin sodium; cloxyquin; colistimethate sodium; colistin sulfate; coumermycin; coumermycin sodium; cyclacillin; cycloserine; dalfopristin; dapsone; daptomycin; demeclocycline; demeclocycline hydrochloride; demecycline; denofungin; diaveridine; dicloxacillin; dicloxacillin sodium; dihydrostreptomycin sulfate; dipyrithione; dirithromycin; doxycycline; doxycycline calcium; doxycycline fosfatex; doxycycline hyclate; droxacin sodium; enoxacin; epicillin; epitetracycline hydrochloride; erythromycin; erythromycin acistrate; erythromycin estolate; erythromycin ethylsuccinate; erythromycin gluceptate; erythromycin lactobionate; erythromycin propionate; erythromycin stearate; ethambutol hydrochloride; ethionamide; fleroxacin; floxacillin; fludalanine; flumequine; fosfomycin; fosfomycin tromethamine; fumoxicillin; furazolium chloride; furazolium tartrate; fusidate sodium; fusidic acid; gentamicin sulfate; gloximonam; gramicidin; haloprogin; hetacillin; hetacillin potassium; hexedine; ibafloxacin; imipenem; isoconazole; isepamicin; isoniazid; josamycin; kanamycin sulfate; kitasamycin; levofuraltadone; levopropylcillin potassium; lexithromycin; lincomycin; lincomycin hydrochloride; lomefloxacin; Lomefloxacin hydrochloride; lomefloxacin mesylate; loracarbef; mafenide; meclocycline; meclocycline sulfosalicylate; megalomicin potassium phosphate; mequidox; meropenem; methacycline; methacycline hydrochloride; methenamine; methenamine hippurate; methenamine mandelate; methicillin sodium; metioprim; metronidazole hydrochloride; metronidazole phosphate; mezlocillin; mezlocillin sodium; minocycline; minocycline hydrochloride; mirincamycin hydrochloride; monensin; monensin sodiumr; nafcillin sodium; nalidixate sodium; nalidixic acid; natainycin; nebramycin; neomycin palmitate; neomycin sulfate; neomycin undecylenate; netilmicin sulfate; neutramycin; nifuiradene; nifuraldezone; nifuratel; nifuratrone; nifurdazil; nifurimide; niflupirinol; nifurquinazol; nifurthiazole; nitrocycline; nitrofurantoin; nitromide; norfloxacin; novobiocin sodium; ofloxacin; onnetoprim; oxacillin; oxacillin sodium; oximonam; oximonam sodium; oxolinic acid; oxytetracycline; oxytetracycline calcium; oxytetracycline hydrochloride; paldimycin; parachlorophenol; paulomycin; pefloxacin; pefloxacin mesylate; penamecillin; penicillin G benzathine; penicillin G potassium; penicillin G procaine; penicillin G sodium; penicillin V; penicillin V benzathine; penicillin V hydrabamine; penicillin V potassium; pentizidone sodium; phenyl aminosalicylate; piperacillin sodium; pirbenicillin sodium; piridicillin sodium; pirlimycin hydrochloride; pivampicillin hydrochloride; pivampicillin pamoate; pivampicillin probenate; polymyxin B sulfate; porfiromycin; propikacin; pyrazinamide; pyrithione zinc; quindecamine acetate; quinupristin; racephenicol; ramoplanin; ranimycin; relomycin; repromicin; rifabutin; rifametane; rifamexil; rifamide; rifampin; rifapentine; rifaximin; rolitetracycline; rolitetracycline nitrate; rosaramicin; rosaramicin butyrate; rosaramicin propionate; rosaramicin sodium phosphate; rosaramicin stearate; rosoxacin; roxarsone; roxithromycin; sancycline; sanfetrinem sodium; sarmoxicillin; sarpicillin; scopafungin; sisomicin; sisomicin sulfate; sparfloxacin; spectinomycin hydrochloride; spiramycin; stallimycin hydrochloride; steffimycin; streptomycin sulfate; streptonicozid; sulfabenz; sulfabenzamide; sulfacetamide; sulfacetamide sodium; sulfacytine; sulfadiazine; sulfadiazine sodium; sulfadoxine; sulfalene; sulfamerazine; sulfameter; sulfamethazine; sulfamethizole; sulfamethoxazole; sulfamonomethoxine; sulfamoxole; sulfanilate zinc; sulfanitran; sulfasalazine; sulfasomizole; sulfathiazole; sulfazamet; sulfisoxazole; sulfisoxazole acetyl; sulfisboxazole diolamine; sulfomyxin; sulopenem; sultamricillin; suncillin sodium; talampicillin hydrochloride; teicoplanin; temafloxacin hydrochloride; temocillin; tetracycline; tetracycline hydrochloride; tetracycline phosphate complex; tetroxoprim; thiamphenicol; thiphencillin potassium; ticarcillin cresyl sodium; ticarcillin disodium; ticarcillin monosodium; ticlatone; tiodonium chloride; tobramycin; tobramycin sulfate; tosufloxacin; trimethoprim; trimethoprim sulfate; trisulfapyrimidines; troleandomycin; trospectomycin sulfate; tyrothricin; vancomycin; vancomycin hydrochloride; virginiamycin; or zorbamycin.

The methods and compounds as described herein are useful for both prophylactic and therapeutic treatment. As used herein the term treating or treatment includes prevention; delay in onset; diminution, eradication, or delay in exacerbation of signs or symptoms after onset; and prevention of relapse. For prophylactic use, a therapeutically effective amount of the compounds and compositions or pharmaceutically acceptable salts thereof as described herein are administered to a subject prior to onset (e.g., before obvious signs of a bacterial infection), during early onset (e.g., upon initial signs and symptoms of a bacterial infection), or after an established inflammatory response or development of a bacterial infection. Prophylactic administration can occur for several days to years prior to the manifestation of symptoms of an infection. Prophylactic administration can be used, for example, in the preventative treatment of subjects exposed to *Staphylococcus aureus*. Therapeutic treatment involves administering to a subject a therapeutically effective amount of the compounds and compositions or pharmaceutically acceptable salts thereof as described herein after a bacterial infection is diagnosed.

Kits

Also provided herein are kits for treating or preventing a bacterial infection in a subject. A kit can include any of the compounds or compositions described herein. For example, a kit can include a compound of Structure S. A kit can further include one or more antibacterial agents (e.g., oxacillin). A kit can include an oral formulation of any of the compounds or compositions described herein. A kit can additionally include directions for use of the kit (e.g., instructions for treating a subject).

The examples below are intended to further illustrate certain aspects of the methods and compounds described herein, and are not intended to limit the scope of the claims.

EXAMPLES

The following examples are set forth below to illustrate the methods, compositions, and results according to the disclosed subject matter. These examples are not intended to be inclusive of all aspects of the subject matter disclosed herein, but rather to illustrate representative methods, compositions, and results. These examples are not intended to exclude equivalents and variations of the present invention, which are apparent to one skilled in the art.

All chemicals were purchased from commercial suppliers and used without further purification. All solvents were dried and distilled before use. Tetrahydrofuran was distilled from sodium/benzophenone. Dichloromethane and acetonitrile were distilled over calcium hydride. Flash column chromatography was performed with silica gel (200-300 mesh). $^1$H NMR spectra were recorded at 400 MHz at ambient temperature. $^{13}$C NMR spectra were recorded at either 50 or 100 MHz at ambient temperature. Infrared spectra were recorded on a spectrophotometer (Perkin-Elmer Spectrum 100). Melting points were determined with melting point apparatus (Fukai X-4). High resolution mess spectra were performed by either FAB or ESI on an Agilent ESI-TOF LC-MS 6200 system. Analytical HPLC was performed on an Agilent 1100 series with diode array detectors and auto samplers. The specifications of HPLC analysis are as follows, Method A: flow rate, 1 mL/min; column, Inertsil SIL, 5 μm, 4.6×250 mm; wavelength, 254 nm; mobile phase, n-hexane/iso-propanol. Method B: flow rate, 1 mL/min; column, Inertsil ODS, 2.5 μm, 4.6×150 mm; wavelength, 215, 254 and 280 nm; mobile phase, A: H$_2$O with 0.1% HCOOH, B: MeOH, gradient of 30-95% B in 25 min. All tested compounds possessed a purity of not less than 95%.

Efforts have been made to ensure accuracy with respect to numbers (e.g., amounts, temperature, etc.) but some errors and deviations should be accounted for. Unless indicated otherwise, temperature is in ° C. or is at ambient temperature, and pressure is at or near atmospheric. There are numerous variations and combinations of reaction conditions, e.g., component concentrations, temperatures, pressures, and other reaction ranges and conditions that can be used to optimize the product purity and yield obtained from the described process. Only reasonable and routine experimentation will be required to optimize such process conditions.

Design of Symmetrical Marinopyrrole Derivatives.

A series of symmetrical marinopyrrole derivatives was designed with substitutions in both ortho- and para-positions of both phenyl rings. Without knowing where these marinopyrroles bind, thoughtful design of derivatives to cover electron-donating and electron-withdrawing groups as well as the size of functional groups can be very beneficial to obtain meaningful SAR information and guide further optimization. Compound 19 was designed and synthesized (Scheme 2) based on the SAR result obtained from compound 1m. Compound 24 bearing two hydroxyl groups in both ortho- and para-positions was designed and synthesized (Scheme 3) to probe if additional hydrogen bond donors are present in both ortho- and para-positions near the protein targets. While the ortho-hydroxyl group was kept constant as critical requirement for activity, a para-substitution using S to connect functional groups for optimization was performed. The same rationale applied for compound 31 possessing two carboxylic acid function groups in para-positions to seek whether hydrogen bond acceptors are present in that positions near the targets. Compound 26 with benzylthio groups in both para-positions was designed to test if potential hydrophobic interactions exist in the extended areas of the para-positions. Methoxy groups in the para-position of benzylthio moiety of 26 were added to generate compound 27, which aimed to probe additional hydrogen bond donors of the targets in further extended areas. Oxidation of 25-27 furnished the corresponding solfones 28-30, which are designed to answer additional questions if the electronic effects of the latter improve the activity and/or whether the terminal groups (COOEt, Ph, 4-MeOPh) have any effects on activity. For the same reason, compound 32 as a sulfone in stead of sulfide was designed to answer additional questions to that from 31. Compound 41 was designed and synthesized (Scheme 4) based on the SAR information obtained from compound 1 (marinopyrrole A) and 1k. As shown in Table 1, compound 1k demonstrated activity against MRSE in the range similar to that of 1 while more potent than that of vancomycin although 1k showed much lower activity against the rest of pathogens.

Synthesis of 2-(Hydroxymethyl)-1'-tosyl-1'H-1,3'-bipyrrole-2'-carbaldehyde (7)

To a solution of (1'-tosyl-1'H-1,3'-bipyrrole-2,2'-diyl)dimethanol 6 obtained from ethyl 3-amino-1H-pyrrole-2-carboxylate hydrochloride 2 in three steps (see Cheng et al) (2.00 g, 5.78 mmol) in DMSO (30 mL) was added IBX (1.78 g, 6.36 mmol) at room temperature. After being stirred for 5 h, the mixture was quenched with water (50 mL). The suspension was filtered and the filtrate was extracted with EtOAc (25 mL×3). The combined organic layers were dried over anhydrous sodium sulfate, filtered and concentrated in vacuum. The residue was purified by flash column chromatography (25% EtOAc/petroleum) to give 7 (1.43 g, 72% yield) as a white solid. $^1$H NMR (400 MHz, CDCl$_3$) δ 2.43 (s, 3H), 2.87 (br, s, 1H), 4.44 (s, 2H), 6.33 (d, J=3.2 Hz, 1H), 6.38 (dd, J=4.0, 2.8 Hz, 1H), 7.05 (s, 1H), 7.09 (dd, J=4.4, 2.0 Hz, 1H), 7.31 (d, J=3.6 Hz, 1H), 7.35 (d, J=8.4 Hz, 2H), 7.82 (d, J=8.4 Hz, 2H), 9.46 (s, 1H) ppm; $^{13}$C NMR (CDCl$_3$, 100 MHz) δ 21.70, 53.00, 111.00, 111.16, 121.55, 123.57, 127.11, 127.11, 127.32, 128.70, 130.24, 130.24, 132.90, 132.99, 135.55, 145.77, 179.27 ppm; HRMS (M+Na$^+$) calcd for C$_{17}$H$_{16}$N$_2$NaO$_4$S, 367.0728. found 367.0733; IR (KBr) 3425, 3118, 2924, 2875, 2730, 1662, 1595, 1369, 1317, 1177, 1086, 1012, 774, 754, 669.

Synthesis of 2-((tert-Butyldimethylsilyloxy)methyl)-1'-tosyl-1'H-1,3'-bipyrrole-2'-carbaldehyde (8)

To a solution of 7 (6.00 g, 17.44 mmol) in dry CH$_2$Cl$_2$ (60 mL) was added imidazole (2.37 g, 34.81 mmol) at room temperature. After being stirred for 5 min, TBDMSCl (5.30 g, 34.82 mmol) was added. The mixture was stirred for about 2.5 h and quenched with water (50 mL) and extracted with CH$_2$Cl$_2$ (25 mL×3). The combined organic layers were dried over anhydrous sodium sulfate, filtered and concentrated in vacuum. The residue was purified by flash column chromatography (20% EtOAc/petroleum) to give 8 (5.59 g, 70% yield) as a white solid. $^1$H NMR (400 MHz, CDCl$_3$) δ −0.04 (s, 6H), 0.82 (s, 9H), 2.42 (s, 3H), 4.61 (s, 2H), 6.34-6.36 (m, 2H), 7.03 (t, J=1.6 Hz, 1H), 7.11 (dd, J=4.0, 1.6 Hz, 1H), 7.26 (d, J=2.4 Hz, 1H), 7.29 (d, J=8.4 Hz, 2H), 7.85 (d, J=8.4 Hz, 2H), 9.46 (s, 1H) ppm; $^{13}$C NMR (CDCl$_3$, 100 MHz) δ −5.67, −5.67, 18.44, 21.65, 25.88, 25.88, 25.88, 53.34, 3737, 3144, 2953, 2929, 2855, 1639, 1603, 1499, 1413, 1375, 1274, 1179, 1158, 1026, 840 cm$^{-1}$.

Synthesis of (4-(Benzyloxy)-2-methoxyphenyl)(2-((tert-butyldimethylsilyloxy)methyl)-1'-tosyl-1'H-1,3'-bipyrrol-2'-yl)methanol (10)

To a solution of 4-(benzyloxy)-1-bromo-2-methoxybenzene (9) (0.80 g, 2.73 mmol) in dry THF (5 mL) at −78° C. under N$_2$ was slowly added n-BuLi (1.09 mL, 2.5 M in n-pentane, 2.73 mmol). After being stirred for 40 min, a solution of 8 (0.50 g, 1.09 mmol) in dry THF (1.5 mL) was added slowly via a syringe. The mixture was stirred for about 1 h and quenched by addition of a saturated aqueous NH$_4$Cl (15 mL) solution and extracted with EtOAc (15 mL×3). The combined organic layers were dried over anhydrous sodium sulfate, filtered and concentrated in vacuum. The residue was purified by flash column chromatography (15% EtOAc/petroleum) to give 10 (0.66 g, 90% yield) as a pale yellow solid. mp 39.3-41.7° C.; $^1$H NMR (400 MHz, CDCl$_3$) δ −0.03 (s, 3H), −0.02 (s, 3H), 0.84 (s, 9H), 2.40 (s, 3H), 2.73 (d, J=5.2 Hz, 1H), 3.68 (s, 3H), 4.38 (d, J=12.0 Hz, 1H), 4.63 (d, J=11.6 Hz, 1H), 5.04 (s, 2H), 5.74 (d, J=5.2 Hz, 1H), 6.02 (t, J=2.0 Hz, 1H), 6.12 (t, J=3.2 Hz, 1H), 6.28 (d, J=3.6 Hz, 1H), 6.47-6.49 (m, 2H), 6.66 (t, J=2.4 Hz, 1H), 7.14-7.17 (m, 2H), 7.28 (d, J=10.4 Hz, 2H), 7.33-7.44 (m, 4H), 7.85 (d, J=8.4 Hz, 2H) ppm; $^{13}$C NMR (CDCl$_3$, 100 MHz) δ −5.70, −5.70, 18.44, 21.49, 25.87, 25.87, 53.07, 55.21, 63.61, 69.97, 99.11, 104.80, 107.70, 107.96, 111.32, 121.26, 123.50, 123.74, 126.97, 126.97, 127.46, 127.46, 127.87, 128.01, 128.31, 128.31, 128.46, 129.21, 129.67, 129.67, 136.36, 136.40, 136.79, 144.84, 157.16, 159.22 ppm; HRMS (M+Na$^+$) calcd for C$_{37}$H$_{44}$N$_2$NaO$_6$SSi, 695.2587. found 695.2598; IR (KBr) 3450, 3032, 2953, 2885, 2855, 1707, 1611, 1591, 1502, 1467, 1376, 1333, 1255, 1180, 1021, 838, 700, 600 cm$^{-1}$.

Synthesis of (4-(Benzyloxy)-2-methoxyphenyl)(2-((tert-butyldimethylsilyloxy)methyl)-1'-tosyl-1'H-1,3'-bipyrrol-2'-yl)methanone (11)

To a solution of 10 (3.67 g, 5.46 mmol) in dry DMSO (40 mL) was added IBX (3.06 g, 10.92 mmol) at room temperature. The mixture was allowed to warm up to 30° C. and stir for about 2 h. The mixture was quenched with water (60 mL) and extracted with EtOAc (25 mL×3). The combined organic layers were dried over anhydrous sodium sulfate, filtered and concentrated in vacuum. The residue was purified by flash column chromatography (15% EtOAc/petroleum) to give 11 (3.00 g, 82% yield) as a pale brown solid. mp 44.7-47.0° C.; $^1$H NMR (400 MHz, CDCl$_3$) δ 0.004 (s, 3H), 0.01 (s, 3H), 0.86 (s, 9H), 2.40 (s, 3H), 3.73 (s, 3H), 4.67 (s, 2H), 5.10 (s, 2H), 6.21 (t, J=3.6 Hz, 1H), 6.30 (d, J=3.6 Hz, 1H), 6.52-6.54 (m, 2H), 6.69 (dd, J=4.0, 1.6 Hz, 1H), 7.06 (s, 1H), 7.17 (d, J=3.6 Hz, 1H), 7.26 (d, J=7.2 Hz, 2H), 7.36-7.46 (m, 6H), 7.84 (d, J=8.4 Hz, 2H) ppm; $^{13}$C NMR (CDCl$_3$, 100 MHz) δ −5.53, −5.53, 18.50, 21.63, 25.96, 25.96, 25.96, 53.61, 55.65, 70.22, 99.68, 104.56, 108.92, 111.55, 121.34, 122.70, 127.03, 127.03, 127.17, 127.62, 127.62, 128.22, 128.69, 128.69, 129.79, 130.04, 130.04, 131.65, 131.65, 132.33, 132.90, 136.45, 136.80, 144.72, 159.28, 161.84, 183.51 ppm; HRMS (M+H$^+$) calcd for C$_{37}$H$_{43}$N$_2$O$_6$SSi, 671.2611. found 671.2607; IR (KBr) 3737, 3144, 2953, 2929, 2855, 1639, 1603, 1499, 1413, 1375, 1274, 1179, 1158, 1026, 840 cm$^{-1}$.

Synthesis of (4-(Benzyloxy)-2-methoxyphenyl)(2-(hydroxymethyl)-1'-tosyl-1'H-1,3'-bipyrrol-2'-yl)methanone (12)

To a solution of 11 (2.92 g, 8.38 mmol) in dry THF (20 mL) was added TBAF (3.41 g, 13.07 mmol) at room temperature. After being stirred for about 5 h at room temperature, the mixture was quenched with water (25 mL) and extracted with EtOAc (15 mL×3). The combined organic layers were dried over anhydrous sodium sulfate, filtered and concentrated in vacuum. The residue was purified by flash column chromatography (25% EtOAc/petroleum) to give 12 (2.30 g, 95% yield) as a white solid. mp 55.7-58.3° C.; $^1$H NMR (400 MHz, CDCl$_3$) δ 2.43 (s, 3H), 3.76 (s, 3H), 4.55 (s, 1H), 5.10 (s, 2H), 5.30 (s, 2H), 6.24 (dd, J=4.0, 2.4 Hz, 1H), 6.31 (d, J=3.6 Hz, 1H), 6.52-6.56 (m, 2H), 6.65 (dd, J=4.0, 1.6 Hz, 1H), 7.00 (t, J=2.4 Hz, 1H), 7.27 (d, J=3.2 Hz, 1H), 7.30-7.45 (m, 8H), 7.84 (d, J=8.4 Hz, 2H) ppm; $^{13}$C NMR (CDCl$_3$, 100 MHz) δ 21.64, 53.17, 55.65, 70.18, 99.70, 104.57, 109.59, 110.96, 121.11, 122.58, 123.35, 127.20, 127.20, 127.55, 127.55, 128.20, 128.21, 128.66, 128.66, 128.90, 130.09, 130.09, 131.47, 132.47, 133.12, 135.81, 136.33, 145.34, 159.15, 161.85, 184.48 ppm; HRMS (M+H$^+$) calcd for C$_{31}$H$_{29}$N$_2$O$_6$S, 557.1746. found 557.1743; IR (KBr) 3436, 2929, 2878, 1603, 1498, 1459, 1367, 1276, 1175, 1115, 1022, 867, 671 cm$^{-1}$.

Synthesis of 2'-(4-(Benzyloxy)-2-methoxybenzoyl)-1'-tosyl-1'H-1,3'-bipyrrole-2-carbaldehyde (13)

To a solution of 12 (2.31 g, 4.20 mmol) in dry DMSO (30 mL) was added IBX (2.33 g, 8.30 mmol) at room temperature. The mixture was allowed to warm up to 50° C. and stir for about 3 h. The mixture was quenched with water (40 mL) and extracted with EtOAc (15 mL×3). The combined organic layers were dried over anhydrous sodium sulfate, filtered and concentrated in vacuum. The residue was purified by flash column chromatography (20% EtOAc/petroleum) to give 13 (2.20 g, 96% yield) as a pale yellow solid. mp 132.7-135.0° C.; $^1$H NMR (400 MHz, CDCl$_3$) δ 2.41 (s, 3H), 3.81 (s, 3H), 4.99 (s, 2H), 6.27-6.30 (m, 2H), 6.45 (d, J=2.0 Hz, 1H), 6.49 (dd, J=8.0, 2.0 Hz, 1H), 6.73 (dd, J=3.6, 1.6 Hz, 1H), 6.98 (dd, J=2.4, 1.6 Hz, 1H), 7.17-7.20 (m, 2H), 7.25-7.26 (m, 3H), 7.34 (d, J=8.4 Hz, 2H), 7.38 (d, J=8.4 Hz, 1H), 7.63 (d, J=3.2 Hz, 1H), 7.88 (d, J=8.4 Hz, 2H), 9.56 (s, 1H) ppm; $^{13}$C NMR (CDCl$_3$, 100 MHz) δ 21.70, 55.65, 70.17, 99.64, 104.78, 110.13, 111.57, 121.95, 122.69, 125.22, 127.62, 127.62, 127.69, 128.04, 128.04, 128.21, 128.68, 128.68, 130.03, 130.03, 131.59, 132.02, 134.07, 134.78, 136.41, 139.25, 145.95, 159.37, 162.13, 177.08, 183.45 ppm; HRMS (M+H$^+$) calcd for C$_{31}$H$_{27}$N$_2$O$_6$S, 555.1590. found 555.1600; IR (KBr) 3454, 3124, 3083, 2872, 2792, 1685, 1633, 1566, 1440, 1347, 1169, 1112, 1026, 763 cm$^{-1}$.

Synthesis of (4-(Benzyloxy)-2-methoxyphenyl)(2-((4-(benzyloxy)-2-methoxyphenyl)(hydroxy)methyl)-1'-tosyl-1'H-1,3'-bipyrrol-2'-yl)methanone (14)

To a solution of 4-(benzyloxy)-1-bromo-2-methoxybenzene (9) (0.31 g, 0.11 mmol) in dry THF (12 mL) at −78° C. under N$_2$ was slowly added n-BuLi (0.43 mL, 2.5 M in n-pentane, 0.11 mmol). After being stirred for 30 min, a solution of 13 (0.24 g, 0.43 mmol) in dry THF (2 mL) was added slowly via a syringe. The mixture was stirred for about 2 h and quenched by addition of a saturated aqueous $NH_4Cl$ (10 mL) solution and extracted with EtOAc (10 mL×3). The combined organic layers were dried over anhydrous sodium sulfate, filtered and concentrated in vacuum. The residue was purified quickly by flash column chromatography (20% EtOAc/petroleum) to give 14 (unstable).

Synthesis of (1'-Tosyl-1'H-1,3'-bipyrrole-2,2'-diyl) bis((4-(benzyloxy)-2-methoxyphenyl)methanone) (15)

To a solution of 14 in dry DMSO (10 mL) was stepwise added IBX (2.40 g, 0.48 mmol) at room temperature. The mixture was allowed to warm up to 50° C. and stir for about 3.5 h. The mixture was quenched with water (15 mL) and extracted with EtOAc (10 mL×3). The combined organic layers were dried over anhydrous sodium sulfate, filtered and concentrated in vacuum. The residue was purified by flash column chromatography (20% EtOAc/petroleum) to give 15 (237 mg, 72% yield two steps) as a pale brown solid. mp 147.9-152.7° C.; $^1$H NMR (400 MHz, $CDCl_3$) δ 2.42 (s, 3H), 3.64 (s, 3H), 3.73 (s, 3H), 4.98 (s, 2H), 5.03 (s, 2H), 5.87 (t, J=3.2 Hz, 1H), 6.28-6.33 (m, 3H), 6.42-6.45 (m, 2H), 6.54 (d, J=2.0 Hz, 1H), 6.72 (t, J=2.0 Hz, 1H), 7.09 (d, J=8.4 Hz, 1H), 7.31-7.46 (m, 14H), 7.84 (d, J=8.4 Hz, 1H) ppm; $^{13}$C NMR ($CDCl_3$, 100 MHz) δ 21.55, 40.76, 55.49, 55.56, 69.75, 69.95, 98.89, 99.58, 103.93, 104.75, 108.56, 111.99, 120.90, 122.10, 122.65, 122.94, 127.18, 127.18, 127.38, 127.38, 128.03, 128.03, 128.08, 128.08, 128.48, 128.48, 128.50, 128.57, 129.47, 129.47, 131.54, 131.78, 132.10, 132.32, 134.01, 135.79, 136.01, 136.22, 144.86, 159.22, 160.38, 161.52, 163.17, 182.48, 183.62 ppm; HRMS (M+H$^+$) calcd for $C_{45}H_{39}N_2O_8S$, 767.2427. found 767.2414; IR (KBr) 3433, 3113, 2937, 2874, 1634, 1599, 1499, 1450, 1265, 1170, 1029, 746, 667, 585 cm$^{-1}$.

Synthesis of (1'-Tosyl-1'H-1,3'-bipyrrole-2,2'-diyl) bis((4-hydroxy-2-methoxyphenyl)methanone) (16)

To a solution of 15 (1.00 g, 1.30 mmol) in a 3:1 mixture of MeOH/EtOAc (10 mL) was added Pd/C (0.54 g, 0.13 mmol, purity: 5%) under 1 atm $H_2$. The mixture was stirred for about 12 h at room temperature. The suspension was filtered and the filtrate was washed with acetone (100 mL). The combined organic layers were concentrated in vacuum and the residue was purified by flash column chromatography (20% acetone/petroleum) to give 16 (0.65 g, 85% yield) as a gray solid. mp 157.3-160.3° C.; $^1$H NMR (400 MHz, $CDCl_3$) δ 2.31 (s, 3H), 3.35 (s, 3H), 3.38 (s, 3H), 5.90 (s, 1H), 5.99 (d, J=8.4 Hz, 1H), 6.05 (s, 1H), 6.20 (d, J=8.0 Hz, 1H), 6.24 (s, 1H), 6.39 (d, J=2.4 Hz, 1H), 6.42 (d, J=2.8 Hz, 1H), 6.74 (s, 1H), 6.94 (d, J=8.0 Hz, 1H), 7.20-7.24 (m, 3H), 7.49 (d, J=3.2 Hz, 1H), 7.85 (d, J=7.6 Hz, 2H), 8.29 (br, s, 1H), 8.88 (br, s, 1H) ppm; $^{13}$C NMR (acetone-d$_6$, 100 MHz) δ 21.52, 55.70, 55.79, 99.45, 100.04, 106.99, 107.75, 109.35, 112.76, 120.50, 122.35, 122.46, 123.34, 128.81, 128.81, 130.01, 130.46, 130.46, 131.23, 132.07, 132.20, 134.03, 134.68, 137.20, 146.06, 160.09, 161.31, 162.12, 163.86, 183.31, 183.35 ppm; HRMS (M+Na$^+$) calcd for $C_{31}H_{26}N_2O_8S$, 609.1308. found 609.1313; IR (KBr) 3422, 2934, 2853, 1606, 1466, 1436, 1313, 1268, 1174, 936, 671 cm$^{-1}$.

Synthesis of 1'H-1,3'-Bipyrrole-2,2'-diylbis((4-hydroxy-2-methoxyphenyl)methanone) (17)

To a solution of 16 (100 mg, 0.17 mmol) in a 1:1 mixture of MeOH/THF (5 mL) was added KOH (39 mg, 0.69 mmol) at room temperature. After being stirred for 2 h, the mixture was adjusted to pH 7.0 with 0.5 N HCl and extracted with EtOAc (10 mL×3). The combined organic layers were dried over anhydrous sodium sulfate, filtered and concentrated in vacuum. The residue was purified by flash column chromatography (50% EtOAc/petroleum) to give 17 (66 mg, 96% yield) as a brown solid. mp 83.0-85.7° C.; $^1$H NMR (400 MHz, $CD_3OD$-d$_4$) δ 3.55 (s, 3H), 3.66 (s, 3H), 6.00 (t, J=2.4 Hz, 1H), 6.09 (dd, J=8.4, 2.0 Hz, 1H), 6.17 (d, J=2.0 Hz, 1H), 6.22 (d, J=2.0 Hz, 1H), 6.33 (dd, J=8.4, 2.0 Hz, 1H), 6.36 (dd, J=4.0, 2.0 Hz, 1H), 6.41 (d, J=2.0 Hz, 1H), 6.83 (s, 1H), 6.99 (d, J=8.4 Hz, 1H), 7.02 (t, J=1.6 Hz, 1H), 7.04 (d, J=8.4 Hz, 1H) ppm; $^{13}$C NMR ($CD_3OD$-d$_4$, 100 MHz) δ 55.69, 55.85, 99.75, 100.10, 106.98, 107.78, 109.96, 110.64, 120.78, 121.46, 124.03, 124.43, 127.17, 132.42, 132.57, 133.67, 133.84 133.96, 160.55, 161.11 162.41, 162.56, 185.53, 185.61 ppm; HRMS (M+H$^+$) calcd for $C_{24}H_{21}N_2O_6$ 433.1400. found 433.1379; IR (KBr) 3293, 2938, 1697, 1610, 1465, 1407, 1308, 1269, 1201, 1163, 1121, 1031, 959, 868, 748 cm$^{-1}$.

Synthesis of (4,4',5,5'-Tetrachloro-1'H-1,3'-bipyrrole-2,2'-diyl)bis((5-chloro-4-hydroxy-2-methoxyphenyl)methanone) (18)

To a solution of 17 (20 mg, 0.046 mmol) in dry MeCN (2 mL) at room temperature was gradually added NCS (37 mg, 0.28 mmol). After being stirred for about 6 h at room temperature, the mixture was quenched with water (15 mL) and extracted with EtOAc (15 mL×3). The combined organic layers were dried over anhydrous sodium sulfate, filtered and concentrated in vacuum. The residue was purified by flash column chromatography (33% EtOAc/petroleum) to give 18 (11 mg, 40% yield) as a yellow solid. mp 102.7-104.7° C.; $^1$H NMR (400 MHz, acetone-d$_6$) δ 3.65 (s, 3H), 3.71 (s, 3H), 6.52 (s, 1H), 6.55 (s, 1H), 6.71 (s, 1H), 7.10 (s, 1H), 7.23 (s, 1H) ppm; $^{13}$C NMR ($CD_3OD$-d$_4$+$CDCl_3$, 100 MHz) δ 55.99, 56.03, 100.22, 100.86, 110.21, 111.77, 111.83, 112.37, 119.31, 120.11, 120.80, 120.86, 124.20, 124.960, 125.98, 130.88, 131.42, 132.46, 157.01, 157.51, 158.39, 159.10, 181.27, 181.86 ppm; HRMS (M+H$^+$) calcd for $C_{24}H_{15}C_{16}N_2O_6$ 636.9061. found 540.9073; IR (KBr) 3441, 3230, 3130, 2936, 2855, 1723, 1628, 1602, 1403, 1298, 1271, 1215, 1037, 994, 745, 666 cm$^{-1}$.

Synthesis of (4,4',5,5'-Tetrachloro-1'H-1,3'-bipyrrole-2,2'-diyl)bis((5-chloro-2,4-dihydroxyphenyl)methanone) (19)

To a solution of 18 (14 mg, 0.02 mmol) in dry $CH_2Cl_2$ (4 mL) was slowly added a solution of BBr$_3$ (19 mg, 0.08 mmol) in dry $CH_2Cl_2$ (1 mL) via a syringe under $N_2$ at −78° C. After being stirred for 0.5 h, the mixture was quenched by addition of water (10 mL) and extracted with $CH_2Cl_2$ (10 mL×3). The combined organic layers were dried over anhydrous sodium sulfate, filtered and concentrated in vacuum. The residue was purified by flash column chromatography (25% EtOAc/petroleum) to give 19 (11 mg, 85% yield) as a pale brown solid. mp 145.7-147.7° C.; $^1$H NMR (400 MHz, $CD_3OD$-d$_4$) δ 6.27 (s, 1H), 6.32 (s, 1H), 7.31 (s, 1H), 7.41 (s, 1H), 7.96 (s, 1H) ppm; $^{13}$C NMR ($CD_3OD$, 100 MHz) δ 101.49, 105.13, 105.25, 110.00, 112.90, 113.27, 114.67, 119.42, 120.24, 123.00, 123.87, 125.98, 130.91, 132.64, 132.66, 133.99, 134.07, 163.85, 164.48, 165.02, 184.46, 185.64 ppm; HRMS (M+Na$^+$) calcd for $C_{22}H_{10}C_{16}N_2NaO_6$ 630.8568. found 630.8581; IR (KBr) 3425, 2961, 2924, 2854, 1654, 1622, 1414, 1384, 1358, 1258, 1024, 800 cm$^{-1}$. HPLC purity, 95.4%.

Synthesis of (1'-Tosyl-1'H-1,3'-bipyrrole-2,2'-diyl)bis(((2-methoxy-4-hydroxytrifluoromethanesulfonate)phenyl)methanone) (20)

To a solution of 16 (0.50 g, 0.85 mmol) in dry MeCN (10 mL) at −30° C. under N$_2$ was slowly added DIPEA (0.44 g, 3.41 mmol). After being stirred for 5 min, Tf$_2$O (0.72 g, 2.60 mmol) was added slowly via a syringe. The mixture was stirred for about 3 h at room temperature and quenched with water (10 mL) and extracted with EtOAc (10 mL×3). The combined organic layers were dried over anhydrous sodium sulfate, filtered and concentrated in vacuum. The residue was purified by flash column chromatography (15% EtOAc/petroleum) to give 20 (0.62 g, 86% yield) as a pale brown solid. mp 116.3-120.0° C.; $^1$H NMR (400 MHz, CDCl$_3$) δ 2.46 (s, 3H), 3.71 (s, 3H), 3.79 (s, 3H), 5.90 (t, J=2.8 Hz, 1H), 6.31 (d, J=2.8 Hz, 1H), 6.38 (d, J=3.2 Hz, 1H), 6.53 (d, J=1.6 Hz, 1H), 6.63 (dd, J=8.4, 1.6 Hz, 1H), 6.70 (s, 1H), 6.80 (s, 1H), 6.83 (d, J=8.4 Hz, 1H), 7.22 (d, J=8.4 Hz, 1H), 7.39 (d, J=8.4 Hz, 3H), 7.67 (d, J=3.6 Hz, 1H), 7.99 (d, J=8.0 Hz, 2H) ppm; $^{13}$C NMR (CDCl$_3$, 100 MHz) δ 21.59, 56.01, 56.10, 104.81, 105.22, 109.65, 111.29, 112.18, 112.23, 117.08, 120.28, 123.86, 126.14, 127.57, 128.07, 128.46, 128.46, 128.97, 129.68, 129.68, 130.45, 131.78, 132.18, 132.70, 134.11, 135.64, 145.44, 150.99, 151.83, 158.38, 159.05, 181.57, 181.98 ppm; HRMS (M+H$^+$) calcd for C$_{33}$H$_{25}$F$_6$N$_2$O$_{12}$S$_3$ 851.0474. found 851.0480; IR (KBr) 3444, 3121, 2950, 2871, 1642, 1600, 1493, 1426, 1269, 1243, 1141, 948 827, 581 cm$^{-1}$.

Synthesis of (4,4',5,5'-Tetrachloro-1'-Tosyl-1'H-1,3'-bipyrrole-2,2'-diyl)bis(((2-methoxy-4-hydroxytrifluoromethanesulfonate)phenyl)methanone) (21)

To a solution of 20 (0.50 g, 0.59 mmol) in dry DMF (10 mL) at room temperature was gradually added NCS (0.51 g, 3.82 mmol). After being stirred for about 3 h at room temperature, the mixture was quenched with water (15 mL) and extracted with EtOAc (15 mL×3). The combined organic layers were dried over anhydrous sodium sulfate, filtered and concentrated in vacuum. The residue was purified by flash column chromatography (12% EtOAc/petroleum) to give 21 (0.20 g, 35% yield) as a yellow solid. mp 81.7-83.3° C.; $^1$H NMR (400 MHz, CD$_3$OD) δ 2.49 (s, 3H), 3.50 (s, 3H), 3.61 (s, 3H), 6.41 (s, 1H), 6.57 (d, J=8.0 Hz, 1H), 6.82 (d, J=2.0 Hz, 1H), 6.90 (d, J=2.0 Hz, 1H), 6.95 (dd, J=8.8, 2.4 Hz, 1H), 7.32 (d, J=8.4 Hz, 1H), 7.51 (d, J=12.0 Hz, 2H), 7.64 (d, J=8.4 Hz, 1H), 7.92 (d, J=8.4 Hz, 2H) ppm; $^{13}$C NMR (CDCl$_3$, 100 MHz) δ 21.61, 55.90, 56.13, 104.61, 105.00, 112.01, 112.54, 113.03, 113.61, 116.93, 119.59, 120.12, 120.80, 125.09, 127.11, 128.01, 128.40, 128.40, 129.32, 129.94, 129.94, 131.06, 131.30, 132.63, 132.86, 133.68, 146.57, 151.94, 152.94, 158.53, 159.68, 180.21, 181.56 ppm; HRMS (M+H$^+$) calcd for C$_{33}$H$_{21}$Cl$_4$N$_2$O$_{12}$S$_3$ 986.8915. found 986.8926; IR (KBr) 3446, 2923, 2853, 1653, 1603, 1491, 1428, 1270, 1216, 1140, 996, 950, 831, 585 cm$^{-1}$.

Synthesis of (4,4',5,5'-Tetrachloro-1'-Tosyl-1'H-1,3'-bipyrrole-2,2'-diyl)bis(((2-hydroxy-4-hydroxytrifluoromethanesulfonate)phenyl)methanone (22)

To a solution of 21 (37 mg, 0.03 mmol) in dry CH$_2$Cl$_2$ (5 mL) was slowly added a solution of BBr$_3$ (56 mg, 0.22 mmol) in dry CH$_2$Cl$_2$ (1 mL) via a syringe under N$_2$ at −78° C. After being stirred for 0.5 h, the mixture was quenched by addition of water (10 mL) and extracted with CH$_2$Cl$_2$ (10 mL×3). The combined organic layers were dried over anhydrous sodium sulfate, filtered and concentrated in vacuum. The residue was purified by flash column chromatography (10% EtOAc/petroleum) to give 22 (28 mg, 78% yield) as a yellow solid. mp 71.3-73.0° C.; $^1$H NMR (400 MHz, CD$_3$OD) δ 2.48 (s, 3H), 6.41 (s, 1H), 6.72-6.95 (m, 4H), 7.35 (d, J=8.0 Hz, 2H), 7.50 (d, J=8.8 Hz, 2H), 7.79 (d, J=8.0 Hz, 2H), 11.28 (br, s, 1H) ppm; $^{13}$C NMR (CDCl$_3$, 100 MHz) δ 21.76, 110.86, 111.12, 111.12, 111.12, 112.21, 112.40, 112.87, 113.93, 116.93, 116.94, 118.33, 118.35, 120.15, 122.32, 125.44, 128.30, 128.30, 130.18, 130.18, 132.90, 134.18, 135.40, 135.42, 135.43, 147.32, 154.40, 163.51, 163.78, 186.18, 188.56 ppm; HRMS (M+H$^+$) calcd for C$_{31}$H$_{17}$Cl$_4$F$_6$N$_2$O$_{12}$S$_3$ 958.8602. found 958.8610; IR (KBr) 3445, 3134, 2920, 2851, 1742, 1631, 1598, 1430, 1385, 1430, 1216, 1140, 970, 842, 583 cm$^{-1}$.

Synthesis of (4,4',5,5'-Tetrachloro-1'H-1,3'-bipyrrole-2,2'-diyl)bis(((2-hydroxy-4-hydroxytrifluoromethanesulfonate)phenyl)methanone) (23)

To a solution of 22 (165 mg, 0.17 mmol) in a 1:1 mixture of MeOH/THF (3 mL) was added KOH (39 mg, 0.69 mmol) at room temperature. After being stirred for 15 min, the mixture was adjusted to pH 7.0 with 0.5 N HCl and extracted with EtOAc (10 mL×3). The combined organic layers were dried over anhydrous sodium sulfate, filtered and concentrated in vacuum. The residue was purified by flash column chromatography (33% EtOAc/petroleum) to give 23 (125 mg, 90.6% yield) as a light yellow solid. mp 65.7-67.7° C.; $^1$H NMR (400 MHz, CDCl$_3$) δ 6.17 (s, 1H), 6.53 (dd, J=7.6, 2.0 Hz, 1H), 6.81 (dd, J=8.8, 2.0 Hz, 1H), 6.87 (d, J=2.4 Hz, 1H), 6.93 (d, J=2.4 Hz, 1H), 7.40 (br, s, 1H), 7.57 (d, J=8.8 Hz, 1H), 9.61 (br, s, 1H), 10.67 (s, 1H), 11.49 (s, 1H) ppm; $^{13}$C NMR (CDCl$_3$, 100 MHz) δ 109.34, 111.21, 111.33, 111.61, 112.44, 113.00, 115.90, 117.01, 118.50, 118.60, 118.89, 120.10, 122.60, 123.61, 124.41, 124.92, 132.11, 135.49, 151.32, 153.72, 154.72, 161.95, 162.77, 164.22, 184.70, 186.90 ppm; HRMS (M+H$^+$) calcd for C$_{24}$H$_{11}$Cl$_4$F$_6$N$_2$O$_{10}$S$_2$ 804.8513. found 804.8529; IR (KBr) 3380, 3264, 1627, 1597, 1497, 1429, 1217, 1139, 1107, 970, 942, 605 cm$^{-1}$. HPLC purity, 96.0%.

Synthesis of (4,4',5,5'-Tetrachloro-1'H-1,3'-bipyrrole-2,2'-diyl)bis((2,4-dihydroxyphenyl)methanone) (24)

To a solution of 23 (5 mg, 0.006 mmol) in DMSO (1 mL) was added a solution of KF (1.1 mg, 0.018 mmol) in water (0.1 mL) at room temperature. After being stirred for about 3 h, the mixture was added with water (5 mL) and extracted with EtOAc (5 mL×3). The combined organic layers were dried over anhydrous sodium sulfate, filtered and concentrated in vacuum. The residue was purified by flash column chromatography (40% EtOAc/petroleum) to give 24 (3.3 mg, 75% yield) as a pale yellow solid. mp 103.3-105.3° C.; $^1$H NMR (400 MHz, acetone-d$_6$) δ 6.10 (s, 1H), 6.19 (dd, J=8.8, 2.4 Hz, 1H), 6.22-6.23 (m, 2H), 6.28 (d, J=8.0 Hz, 1H), 7.62 (d, J=8.8 Hz, 1H), 8.09 (br, s, 1H), 12.03 (br, s, 1H) ppm; $^{13}$C NMR (CDCl$_3$, 100 MHz) δ 103.19, 103.49, 107.73, 108.14, 108.30, 108.35, 109.60, 111.44, 113.20, 113.77, 114.26, 115.07, 120.82, 123.89, 126.11, 134.16, 137.03, 162.89, 165.67, 166.61, 167.02, 185.94 ppm; HRMS (M+H$^+$) calcd for C$_{22}$H$_{13}$Cl$_4$N$_2$O$_6$ 540.9528. found 540.9536; IR (KBr) 3400, 3282, 2958, 2922, 2851, 1626, 1596, 1447, 1333, 1266, 1177, 978, 796 cm$^{-1}$. HPLC purity, 98.2%.

Synthesis of (4,4',5,5'-Tetrachloro-1'H-1,3'-bipyrrole-2,2'-diyl)bis(((2-hydroxy-4-(-ethylacetate)thiophenyl)methanone) (25)

Under N$_2$, 23 (50 mg, 0.06 mmol), ethyl 2-mercaptoacetate (33 mg, 0.24 mmol), Pd$_2$(dba)$_3$ (2 mg, 0.003 mmol), Xantphos (4 mg, 0.006 mmol) and i-Pr$_2$NEt (31 mg, 24 mmol) were dissolved in 1,4-dioxane (5 mL). The mixture was heated to reflux and stirred for about 10 h. The mixture was quenched with water (10 mL) and extracted with EtOAc (15 mL×3). The combined organic layers were dried over anhydrous sodium sulfate, filtered and concentrated in vacuum. The residue was purified by flash column chromatography (33% EtOAc/petroleum) to give 25 (28 mg, 61% yield) as a yellow solid. mp 51.3-53.3° C.; $^1$H NMR (400 MHz, CDCl$_3$) δ 1.24-1.29 (m, 6H), 3.71 (s, 2H), 3.76 (s, 2H), 4.19-4.25 (m, 4H), 6.11 (s, 1H), 6.46 (d, J=8.4 Hz, 1H), 6.73 (d, J=8.0 Hz, 1H), 6.80 (d, J=9.6 Hz, 2H), 7.20 (br, s, 1H), 7.37 (br, s, 1H), 10.51 (br, s, 1H), 10.93 (s, 1H), 11.58 (s, 1H) ppm; $^{13}$C NMR (CDCl$_3$, 100 MHz) δ 14.01, 14.01, 33.92, 34.17, 62.05, 62.09, 108.68, 111.90, 113.64, 114.13, 116.27, 116.27, 116.47, 116.80, 116.93, 121.32, 122.17, 124.17, 124.62, 130.62, 133.37, 147.17, 148.83, 161.82, 162.94, 168.61, 168.70, 185.14, 186.83 ppm; HRMS (M+H$^+$) calcd for C$_{30}$H$_{25}$Cl$_4$N$_2$O$_8$S$_2$ 744.9806. found 744.9812; IR (KBr) 3671, 3368, 3080, 2960, 2920, 1919, 1735, 1618, 1585, 1439, 1216, 1145, 1030, 745, 703 cm$^{-1}$. HPLC purity, 96.8%.

Synthesis of (4,4',5,5'-Tetrachloro-1'H-1,3'-bipyrrole-2,2'-diyl)bis(((2-hydroxy-4-benzylthio)phenyl)methanone) (26)

Under N$_2$, 23 (50 mg, 0.06 mmol), phenylmethanethiol (32 mg, 0.24 mmol), Pd$_2$(dba)$_3$ (2 mg, 0.003 mmol), Xantphos (4 mg, 0.006 mmol) and i-Pr$_2$NEt (31 mg, 24 mmol) were dissolved in 1,4-dioxane (5 mL). The mixture was heated to reflux and stirred for about 4 h. The mixture was quenched with water (10 mL) and extracted with EtOAc (15 mL×3). The combined organic layers were dried over anhydrous sodium sulfate, filtered and concentrated in vacuum. The residue was purified by flash column chromatography (15% EtOAc/petroleum) to give 26 (45 mg, 96% yield) as a yellow solid. mp 81.7-83.7° C.; $^1$H NMR (400 MHz, CDCl$_3$) δ 4.17 (s, 2H), 4.22 (s, 2H), 6.11 (s, 1H), 6.47 (d, J=8.4 Hz, 1H), 6.61 (br, s, 1H), 6.74 (s, 1H), 6.80 (s, 1H), 7.27-7.41 (m, 12H), 9.90 (br, s, 1H), 10.95 (s, 1H), 11.63 (s, 1H) ppm; $^{13}$C NMR (CDCl$_3$, 100 MHz) δ 36.24, 36.43, 108.77, 111.98, 113.35, 113.85, 115.84, 116.15, 116.26, 116.79, 117.01, 121.27, 122.15, 124.21, 124.72, 127.65, 127.65, 127.68, 127.68, 128.68, 128.68, 128.68, 128.78, 128.78, 128.78, 128.78, 130.46, 133.14, 135.34, 135.49, 149.49, 151.08, 161.84, 163.04, 185.08, 186.71 ppm; HRMS (M+H$^+$) calcd for C$_{36}$H$_{25}$Cl$_4$N$_2$O$_4$S$_2$ 753.0010. found 753.0005; IR (KBr) 3410, 3236, 3061, 3028, 2923, 1616, 1581, 1483, 1448, 1391, 1327, 1223, 1073, 928, 780 cm$^{-1}$. HPLC purity, 96.9%.

Synthesis of (4,4',5,5'-Tetrachloro-1'H-1,3'-bipyrrole-2,2'-diyl)bis(((2-hydroxy-4-(4-methoxybenzylthio)phenyl)methanone) (27)

Under N$_2$, 23 (20 mg, 0.025 mmol), (4-methoxyphenyl)methanethiol (15 mg, 0.10 mmol), Pd$_2$(dba)$_3$ (0.8 mg, 0.001 mmol), Xantphos (1.6 mg, 0.002 mmol) and i-Pr$_2$NEt (12 mg, 0.10 mmol) were dissolved in 1,4-dioxane (3 mL). The mixture was heated to reflux and stirred for about 4 h. The mixture was quenched with water (10 mL) and extracted with EtOAc (10 mL×3). The combined organic layers were dried over anhydrous sodium sulfate, filtered and concentrated in vacuum. The residue was purified by flash column chromatography (20% EtOAc/petroleum) to give 27 (17 mg, 85% yield) as a yellow solid. mp 84.7-86.7° C.; $^1$H NMR (400 MHz, CDCl$_3$) δ 3.78 (s, 3H), 3.79 (s, 3H), 4.13 (s, 2H), 4.18 (s, 2H), 6.11 (s, 1H), 6.46 (d, J=8.4 Hz, 1H), 6.62 (s, 1H), 6.74 (s, 1H), 6.80 (s, 1H), 6.86 (dd, J=8.4, 3.2 Hz, 5H), 7.31 (t, J=8.4 Hz, 5H), 9.71 (br, s, 1H), 10.99 (s, 1H), 11.64 (s, 1H), ppm; $^{13}$C NMR (CDCl$_3$, 100 MHz) δ 35.72, 35.90, 53.66, 55.25, 108.83, 111.94, 113.30, 113.83, 114.18, 114.18, 114.18, 114.18, 114.18, 115.78, 116.11, 116.24, 116.72, 117.01, 121.23, 121.96, 124.08, 124.77, 127.11, 127.29, 129.85, 129.85, 129.96, 129.96, 130.40, 133.12, 149.68, 151.31, 159.01, 159.06, 161.90, 163.05, 185.02, 186.71 ppm; HRMS (M+H$^+$) calcd for C$_{38}$H$_{29}$Cl$_4$N$_2$O$_6$S$_2$ 813.0221. found 813.0228; IR (KBr) 3421, 3253, 2929, 2836, 1702, 1615, 1511, 1447, 1393, 1329, 1248, 1177, 1075, 1034, 943 cm$^{-1}$. HPLC purity, 96.5%.

Synthesis of (4,4',5,5'-Tetrachloro-1'H-1,3'-bipyrrole-2,2'-diyl)bis(((2-hydroxy-4-(-ethylacetate)sulfonylphenyl)methanone) (28)

To a solution of 25 (22 mg, 0.03 mmol) in CH$_2$Cl$_2$ (2 mL) was added a solution of m-CPBA (31 mg, 0.18 mmol) in CH$_2$Cl$_2$ (1 mL) at room temperature. After being stirred for about 20 h, the mixture was quenched by addition water (10 mL) and extracted with CH$_2$Cl$_2$ (10 mL×3). The combined organic layers were dried over anhydrous sodium sulfate, filtered and concentrated in vacuum. The residue was purified by flash column chromatography (20% acetone, 27% EtOAc, 53% petroleum) to give 28 (16.7 mg, 70% yield) as a yellow solid. mp 89.7-91.7° C.; $^1$H NMR (400 MHz, acetone-d$_6$) δ 1.16-1.18 (m, 6H), 4.09-4.14 (m, 4H), 4.33 (s, 2H), 4.42 (s, 2H), 6.48 (s, 1H), 7.32 (d, J=8.0 Hz, 1H), 7.45-7.52 (m, 3H), 7.61 (d, J=8.0 Hz, 1H), 7.23 (d, J=8.0 Hz, 1H), 10.48 (br, s, 2H), 12.33 (br, s, 2H) ppm; $^{13}$C NMR (acetone-d$_6$, 100 MHz) δ 14.14, 14.14, 60.98, 61.02, 62.58, 62.58, 110.42, 112.21, 117.11, 117.38, 118.94, 119.29, 119.65, 122.89, 124.02, 126.06, 127.21, 128.65, 128.75, 129.08, 131.08, 132.87, 144.04, 144.64, 157.98, 158.59, 163.00, 163.05, 183.41, 184.48 ppm; HRMS (M+H$^+$) calcd for C$_{30}$H$_{25}$Cl$_4$N$_2$O$_{12}$S$_2$ 808.9603. found 808.9599; IR (KBr) 2918, 2850, 2490, 1741, 1637, 1589, 1441, 1407, 1330, 1269, 1215, 1151, 1029, 751, 703, 637 cm$^{-1}$. HPLC purity, 98.1%.

Synthesis of (4,4',5,5'-Tetrachloro-1'H-1,3'-bipyrrole-2,2'-diyl)bis(((2-hydroxy-4-benzylsulfonyl)phenyl)methanone) (29)

To a solution of 26 (30 mg, 0.04 mmol) in CH$_2$Cl$_2$ (2 mL) was added a solution of m-CPBA (42 mg, 0.24 mmol) in CH$_2$Cl$_2$ (1 mL) at room temperature. After being stirred for about 5 h, the mixture was quenched by addition water (10 mL) and extracted with CH$_2$Cl$_2$ (10 mL×3). The combined organic layers were dried over anhydrous sodium sulfate, filtered and concentrated in vacuum. The residue was purified by flash column chromatography (20% acetone, 27% EtOAc, 53% petroleum) to give 29 (24 mg, 75% yield) as a yellow solid. mp 130.7-132.7° C.; $^1$H NMR (400 MHz, CDCl$_3$) δ 4.26 (s, 2H), 4.34 (s, 2H), 6.12 (s, 1H), 6.99 (d, J=8.4 Hz, 1H), 7.05 (d, J=8.4 Hz, 1H), 7.14-7.17 (m, 4H), 7.29-7.37 (m, 8H), 7.58 (d, J=8.4 Hz, 1H), 7.68 (d, J=8.0 Hz, 1H) ppm; $^{13}$C NMR (CDCl$_3$, 100 MHz) δ 62.17, 62.35, 110.30, 110.34, 112.10, 117.23, 117.51, 118.83, 119.18, 119.80, 124.03, 126.02, 127.12, 127.83, 128.40, 128.75, 129.07, 129.07, 129.15, 129.15, 129.19, 129.19, 129.34, 129.40, 129.45, 129.45, 131.25, 131.88, 131.88, 131.88, 131.98, 131.98, 132.82, 144.07, 144.21, 158.24, 183.74, 184.70 ppm; HRMS (M'H$^+$) calcd for C$_{36}$H$_{25}$Cl$_4$N$_2$O$_8$S$_2$ 816.9806. found 816.9800; IR (KBr) 3078, 3030, 2959, 2920, 2851, 2583, 1730, 1636, 1591, 1142, 1407, 1319, 1149, 1125, 879, 750, 701, 628 cm$^{-1}$. HPLC purity, 97.1%.

Synthesis of (4,4',5,5'-Tetrachloro-1'H-1,3'-bipyrrole-2,2'-diyl)bis(((2-hydroxy-4-(4-methoxybenzylsulfonyl)phenyl)methanone) (30)

To a solution of 27 (60 mg, 0.074 mmol) in CH$_2$Cl$_2$ (5 mL) was added a solution of m-CPBA (128 mg, 0.74 mmol) in CH$_2$Cl$_2$ (2 mL) at room temperature. After being stirred for about 20 h, the mixture was quenched by adding water (10 mL) and extracted with CH$_2$Cl$_2$ (10 mL×3). The combined organic layers were dried over anhydrous sodium sulfate, filtered and concentrated in vacuum. The residue was purified by flash column chromatography (20% acetone, 27% EtOAc, 53% petroleum) to give 30 (42 mg, 65% yield) as a yellow solid. mp 104.3-106.3° C.; $^1$H NMR (400 MHz, CDCl$_3$) δ 3.77 (s, 6H), 4.20 (s, 2H), 4.31 (s, 2H), 6.17 (s, 1H), 6.80 (t, J=7.2 Hz, 4H), 6.97 (d, J=8.4 Hz, 1H), 7.05 (d, J=8.4 Hz, 5H), 7.16 (s, 1H), 7.36 (s, 1H), 7.62 (d, J=8.4 Hz, 1H), 7.67 (d, J=8.0 Hz, 1H), 10.44 (br, s, 1H), 11.00 (br, s, 1H) ppm; $^{13}$C NMR (CDCl$_3$, 100 MHz) δ 55.26, 55.26, 61.84, 61.84, 109.45, 112.63, 114.18, 114.18, 114.18, 114.22, 114.22, 117.59, 118.33, 118.57, 118.57, 118.82, 118.93, 122.16, 122.80, 123.45, 124.62, 125.25, 126.44, 131.09, 132.02, 132.02, 132.02, 132.09, 132.09, 133.78, 143.91, 144.84, 160.15, 160.22, 160.63, 161.77, 184.85, 187.06 ppm; HRMS (M+Na$^+$) calcd for C$_{38}$H$_{28}$Cl$_4$N$_2$NaO$_{10}$S$_2$ 898.9837. found 898.9838; IR (KBr) 2961, 2920, 2850, 1730, 1632, 1592, 1512, 1444, 1257, 1148, 1099, 1030, 798 cm$^{-1}$. HPLC purity, 95.1%.

Synthesis of (4,4',5,5'-Tetrachloro-1'H-1,3'-bipyrrole-2,2'-diyl)bis(((2-hydroxy-4-(-acetic acid)thiophenyl)methanone) (31)

To a solution of 25 (20 mg, 0.026 mmol) in a 1:2 mixture of H$_2$O/THF (3 mL) was added LiOH (15 mg, 0.35 mmol) at room temperature. The mixture was allowed to warm up to 50° C. and stir for about 10 h. The mixture was adjusted to pH 5.0 with 0.5 N HCl and extracted with EtOAc (5 mL×3). The combined organic layers were dried over anhydrous sodium sulfate, filtered and concentrated in vacuum. The residue was purified by reverse column chromatography (7% AcOH, 22% H$_2$O, 71% MeOH) to give 31 (15.7 mg, 85% yield) as a brown solid. mp 137.7-139.7° C.; $^1$H NMR (400 MHz, DMSO-d$_6$) δ 3.46 (s, 2H), 3.65 (s, 2H), 6.03 (s, 1H), 6.53-6.60 (m, 3H), 6.64 (s, 1H), 7.38 (d, J=7.6 Hz, 1H), 7.85 (d, J=8.0 Hz, 1H) ppm; $^{13}$C NMR (DMSO-d$_6$, 100 MHz) δ 36.10, 36.80, 108.30, 109.39, 112.71, 112.94, 115.56, 116.02, 116.84, 118.22, 120.95, 122.60, 123.09, 124.39, 128.56, 131.13, 132.65, 133.61, 144.10, 149.87, 159.26, 160.70, 171.50, 172.90, 181.57, 186.55 ppm; HRMS (M+Na$^+$) calcd for C$_{26}$H$_{16}$Cl$_4$N$_2$NaO$_8$S$_2$710.9000. found 710.9009; IR (KBr) 3392, 2955, 2918, 2849, 1592, 1382, 1223, 1023, 671 cm$^{-1}$. HPLC purity, 98.7%.

Synthesis of (4,4',5,5'-Tetrachloro-1'H-1,3'-bipyrrole-2,2'-diyl)bis(((2-hydroxy-4-(-acetic acid)sulfonylphenyl)methanone) (32)

To a solution of 28 (70 mg, 0.086 mmol) in a 1:2 mixture of H$_2$O/THF (5 mL) was added LiOH (49 mg, 1.13 mmol) at room temperature. The mixture was allowed to warm up to 50° C. and stir for about 3 h. The mixture was adjusted to pH 5.0 with 0.5 N HCl and extracted with EtOAc (10 mL×3). The combined organic layers were dried over anhydrous sodium sulfate, filtered and concentrated in vacuum. The residue was purified by reverse column chromatography (4% AcOH, 38% H$_2$O, 58% MeOH) to give 32 (62 mg, 95% yield) as a yellow solid. mp 142.7-144.7° C.; $^1$H NMR (400 MHz, DMSO-d$_6$) δ 4.12 (s, 2H), 4.18 (s, 2H), 6.22 (s, 1H), 7.15 (d, J=8.0 Hz, 1H), 7.27-7.29 (m, 4H), 7.36-7.40 (m, 1H) ppm; $^{13}$C NMR (acetone-d$_6$, 100 MHz) δ 52.09, 52.09, 100.10, 100.18, 100.98, 105.79, 107.20, 108.26, 108.65, 112.73, 113.40, 115.44, 118.90, 118.91, 120.25, 120.40, 120.53, 121.64, 133.09, 146.18, 146.89, 154.58, 163.09, 163.09, 171.58, 172.34 ppm; HRMS (M+H$^+$) calcd for C$_{26}$H$_{17}$Cl$_4$N$_2$O$_{12}$S$_2$ 752.8977. found 752.8981; IR (KBr) 3395, 2957, 2923, 1628, 1445, 1407, 1313, 1147, 1026, 1000, 906, 825, 701 cm$^{-1}$. HPLC purity, 95.2%.

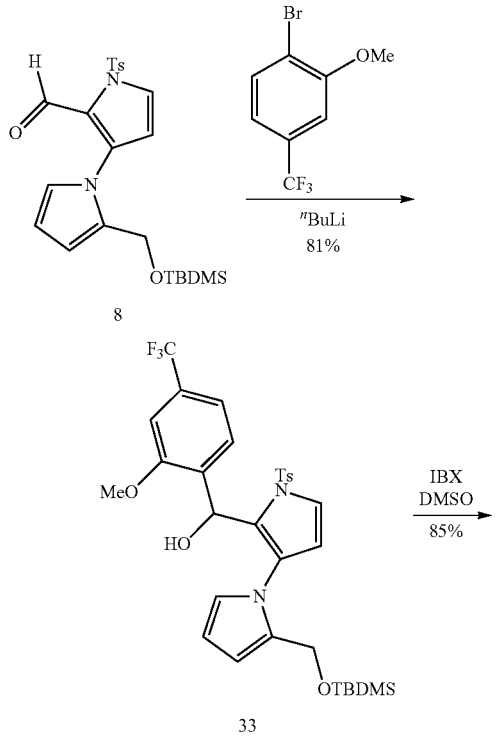

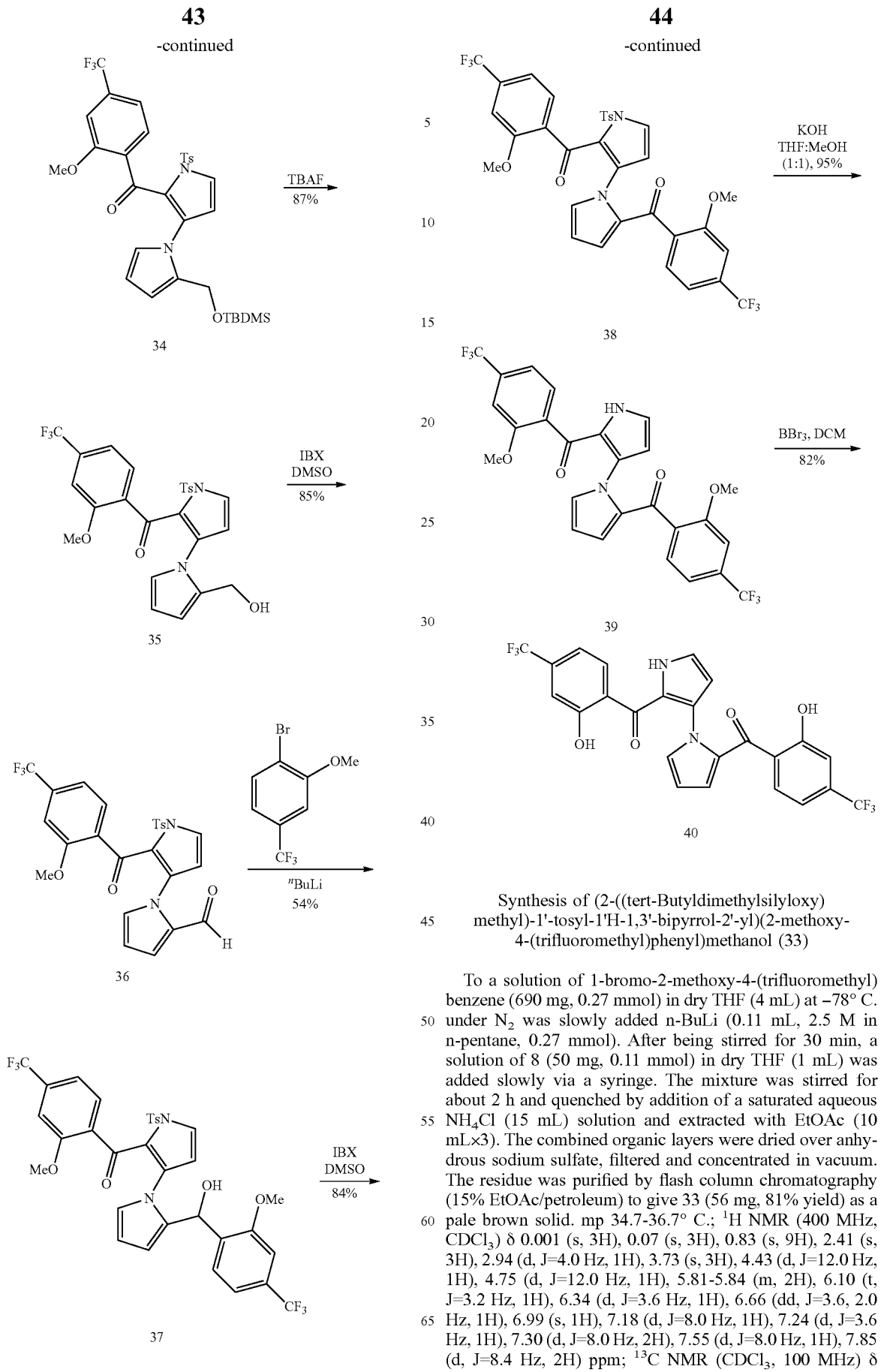

Synthesis of (2-((tert-Butyldimethylsilyloxy) methyl)-1'-tosyl-1'H-1,3'-bipyrrol-2'-yl)(2-methoxy-4-(trifluoromethyl)phenyl)methanol (33)

To a solution of 1-bromo-2-methoxy-4-(trifluoromethyl) benzene (690 mg, 0.27 mmol) in dry THF (4 mL) at −78° C. under $N_2$ was slowly added n-BuLi (0.11 mL, 2.5 M in n-pentane, 0.27 mmol). After being stirred for 30 min, a solution of 8 (50 mg, 0.11 mmol) in dry THF (1 mL) was added slowly via a syringe. The mixture was stirred for about 2 h and quenched by addition of a saturated aqueous $NH_4Cl$ (15 mL) solution and extracted with EtOAc (10 mL×3). The combined organic layers were dried over anhydrous sodium sulfate, filtered and concentrated in vacuum. The residue was purified by flash column chromatography (15% EtOAc/petroleum) to give 33 (56 mg, 81% yield) as a pale brown solid. mp 34.7-36.7° C.; $^1$H NMR (400 MHz, $CDCl_3$) δ 0.001 (s, 3H), 0.07 (s, 3H), 0.83 (s, 9H), 2.41 (s, 3H), 2.94 (d, J=4.0 Hz, 1H), 3.73 (s, 3H), 4.43 (d, J=12.0 Hz, 1H), 4.75 (d, J=12.0 Hz, 1H), 5.81-5.84 (m, 2H), 6.10 (t, J=3.2 Hz, 1H), 6.34 (d, J=3.6 Hz, 1H), 6.66 (dd, J=3.6, 2.0 Hz, 1H), 6.99 (s, 1H), 7.18 (d, J=8.0 Hz, 1H), 7.24 (d, J=3.6 Hz, 1H), 7.30 (d, J=8.0 Hz, 2H), 7.55 (d, J=8.0 Hz, 1H), 7.85 (d, J=8.4 Hz, 2H) ppm; $^{13}$C NMR ($CDCl_3$, 100 MHz) δ

−5.71, −5.67, 18.53, 21.56, 25.92, 25.92, 53.27, 55.53, 62.79, 106.87, 106.91, 108.05, 108.43, 111.37, 117.21, 117.25, 121.56, 123.91, 126.96, 127.01, 127.35, 128.40, 129.44, 129.87, 134.75, 134.76, 135.81, 136.29, 145.17, 156.02 ppm; HRMS (M+Na$^+$) calcd for C$_{31}$H$_{37}$F$_3$N$_2$NaO$_5$SSi 657.2042. found 657.2040; IR (KBr) 3383, 3146, 2956, 2929, 2857, 1734, 1594, 1465, 1415, 1377, 1329, 1241, 1175, 1123, 1032, 841, 778, 670 cm$^{-1}$.

Synthesis of (2-((tert-Butyldimethylsilyloxy)methyl)-1'-tosyl-1'H-1,3'-bipyrrol-2'-yl)(2-methoxy-4-(trifluoromethyl)phenyl)methanone (34)

To a solution of 33 (463 mg, 0.73 mmol) in dry DMSO (10 mL) was added IBX (408 mg, 1.46 mmol) at room temperature. The mixture was allowed to warm up to 50° C. and stir additionally for about 3.5 h. The mixture was quenched with water (15 mL) and extracted with EtOAc (10 mL×3). The combined organic layers were dried over anhydrous sodium sulfate, filtered and concentrated in vacuum. The residue was purified by flash column chromatography (15% EtOAc/petroleum) to give 34 (403 mg, 85% yield) as a pale brown solid. mp 38.0-40.3° C.; $^1$H NMR (400 MHz, CDCl$_3$) δ −0.006 (s, 6H), 0.85 (s, 9H), 2.40 (s, 3H), 3.82 (s, 3H), 4.68 (s, 3H), 6.23 (dd, J=4.0, 2.4 Hz, 1H), 6.33 (d, J=3.6 Hz, 1H), 6.64 (dd, J=4.0, 1.6 Hz, 1H), 7.09 (t, J=2.0 Hz, 1H), 7.21-7.23 (m, 2H), 7.28 (d, J=8.0 Hz, 2H), 7.40 (d, J=8.0 Hz, 1H), 7.85 (d, J=8.4 Hz, 2H) ppm; $^{13}$C NMR (CDCl$_3$, 100 MHz) δ −5.65, −5.65, 18.42, 21.55, 25.65, 25.86, 25.86, 53.48, 55.86, 108.06, 108.09, 109.50, 111.33, 116.83, 116.87, 121.33, 123.91, 127.00, 127.66, 129.27, 129.38, 129.77, 131.85, 132.60, 132.93, 132.99, 133.48, 136.64, 144.82, 157.03, 182.61 ppm; HRMS (M+Na$^+$) calcd for C$_{31}$H$_{35}$F$_3$N$_2$NaO$_5$SSi, 655.1886. found 655.1893; IR (KBr) 3145, 2955, 2929, 2856, 1737, 1647, 1598, 1499, 1463, 1411, 1376, 1328, 1245, 1176, 1130, 1077, 894, 838, 670 cm$^{-1}$.

Synthesis of (2-(Hydroxymethyl)-1'-tosyl-1'H-1,3'-bipyrrol-2'-yl)(2-methoxy-4-(trifluoromethyl)phenyl)methanone (35)

To a solution of 34 (400 mg, 0.63 mmol) in dry THF (10 mL) was added TBAF (495 mg, 1.90 mmol) at room temperature. After being stirred for about 5 h at room temperature, the mixture was quenched with water (10 mL) and extracted with EtOAc (10 mL×3). The combined organic layers were dried over anhydrous sodium sulfate, filtered and concentrated in vacuum. The residue was purified by flash column chromatography (20% EtOAc/petroleum) to give 35 (290 mg, 87% yield) as a light yellow solid. mp 53.3-56.0° C.; $^1$H NMR (400 MHz, CDCl$_3$) δ 2.35 (s, 3H), 2.98 (t, J=6.4 Hz, 1H), 3.76 (s, 3H), 4.54 (d, J=6.8 Hz, 2H), 6.24 (t, J=3.6 Hz, 1H), 6.34 (d, J=6.8 Hz, 1H), 6.61 (dd, J=3.6, 1.2 Hz, 1H), 7.04 (s, 1H), 7.14 (s, 1H), 7.22 (d, J=3.6 Hz, 1H), 7.26-7.30 (m, 3H), 7.38 (d, J=8.0 Hz, 1H), 7.84 (d, J=8.4 Hz, 2H) ppm; $^{13}$C NMR (CDCl$_3$, 100 MHz) δ 21.56, 53.09, 55.92, 108.14, 108.17, 110.27, 110.92, 116.94, 116.97, 122.31, 124.59, 127.16, 128.46, 128.55, 129.15, 130.11, 132.03, 132.68, 132.89, 133.00, 133.74, 135.81, 145.48, 157.03, 183.56 ppm; HRMS (M+Na$^+$) calcd for C$_{25}$H$_{21}$F$_3$N$_2$NaO$_5$S, 541.1021. found 541.1027; IR (KBr) 3425, 3119, 2956, 2925, 1642, 1596, 1500, 1460, 1411, 1328, 1175, 1133, 1078, 893, 673, 602 cm$^{-1}$.

Synthesis of 2'-(2-Methoxy-4-(trifluoromethyl)benzoyl)-1'-tosyl-1'H-1,3'-bipyrrole-2-carbaldehyde (36)

To a solution of 35 (286 mg, 0.55 mmol) in dry DMSO (10 mL) was added IBX (309 mg, 1.10 mmol) at room temperature. After being stirred for about 3.5 h, the mixture was quenched with water (15 mL) and extracted with EtOAc (10 mL×3). The combined organic layers were dried over anhydrous sodium sulfate, filtered and concentrated in vacuum. The residue was purified by flash column chromatography (20% EtOAc/petroleum) to give 36 (242 mg, 85% yield) as a light brown solid. mp 114.3-117.0° C.; $^1$H NMR (400 MHz, CDCl$_3$) δ 2.43 (s, 3H), 3.80 (s, 3H), 6.29 (t, J=3.2 Hz, 1H), 6.48 (d, J=3.6 Hz, 1H), 6.63 (d, J=2.4 Hz, 1H), 7.03 (s, 1H), 7.13 (s, 1H), 7.24 (d, J=7.6 Hz, 1H), 7.35 (d, J=8.0 Hz, 2H), 7.46 (d, J=7.6 Hz, 1H), 7.69 (d, J=3.2 Hz, 1H), 7.89 (d, J=8.4 Hz, 2H), 9.70 (s, 1H) ppm; $^{13}$C NMR (CDCl$_3$, 100 MHz) δ 21.63, 55.89, 108.12, 108.15, 110.55, 111.54, 116.88, 116.92, 123.99, 125.49, 127.53, 127.90, 127.90, 129.62, 130.08, 130.08, 132.34, 132.63, 132.81, 133.15, 134.75, 138.21, 146.08, 177.23, 182.75 ppm; HRMS (M+Na$^+$) calcd for C$_{25}$H$_{19}$F$_3$N$_2$NaO$_5$S, 539.0864. found 539.0856; IR (KBr) 3433, 3141, 3089, 2927, 2855, 1679, 1641, 1562, 1408, 1327, 1173, 1128, 1023, 901, 812, 670 cm$^{-1}$.

Synthesis of (2-(Hydroxy(2-methoxy-4-(trifluoromethyl)phenyl)methyl)-1'-tosyl-1'H-1,3'-bipyrrol-2'-yl)(2-methoxy-4-(trifluoromethyl)phenyl)methanone (37)

To a solution of 1-bromo-2-methoxy-4-(trifluoromethyl)benzene (720 mg, 2.88 mmol) in dry THF (5 mL) at −78° C. under N$_2$ was slowly added n-BuLi (1.15 mL, 2.5 M in n-pentane, 2.88 mmol). After being stirred for 30 min, a solution of 36 (550 mg, 1.06 mmol) in dry THF (1 mL) was added slowly via a syringe. The mixture was stirred for about 2 h and quenched by addition of a saturated aqueous NH$_4$Cl (15 mL) solution and extracted with EtOAc (10 mL×3). The combined organic layers were dried over anhydrous sodium sulfate, filtered and concentrated in vacuum. The residue was purified by flash column chromatography (15% EtOAc/petroleum) to give 37 (400 mg, 54% yield) as a light yellow solid. $^1$H NMR (400 MHz, CDCl$_3$) δ 2.44 (s, 3H), 3.59 (br s, 3H), 3.84 (s, 3H), 5.77 (br s, 1H), 6.17-6.32 (m, 3H), 6.49 (br s, 1H), 6.70 (br s, 1H), 6.83 (d, J=7.6 Hz, 1H), 7.13 (br s, 1H), 7.21 (br s, 1H), 7.35-7.37 (m, 4H), 7.42 (d, J=2.8 Hz, 1H), 7.92 (d, J=8.0 Hz, 2H) ppm; $^{13}$C NMR (CDCl$_3$, 100 MHz) δ 21.67, 55.75, 55.88, 67.96, 105.60, 105.64, 108.13, 108.03, 111.28, 116.78, 116.78, 116.78, 120.85, 120.85, 124.97, 126.20, 127.10, 127.30, 127.63, 127.63, 129.14, 129.14, 129.98, 129.98, 132.50, 132.56, 133.21, 133.45, 135.92, 145.38, 155.48, 157.01, 180.50 ppm; IR (KBr) 3444, 3137, 2923, 1668, 1562, 1447, 1361, 1180, 1014, 752, 668 cm$^{-1}$.

Synthesis of (1'-Tosyl-1'H-1,3'-bipyrrole-2,2'-diyl)bis((2-methoxy-4-(trifluoromethyl)phenyl)methanone) (38)

To a solution of 37 (800 mg, 1.16 mmol) in dry DMSO (20 mL) was gradually added IBX (810 mg, 2.89 mmol) at room temperature. After being stirred for about 1 h, the mixture was quenched with water (30 mL) and extracted with EtOAc (15 mL×3). The combined organic layers were dried over anhydrous sodium sulfate, filtered and concentrated in vacuum. The residue was purified by flash column chromatography (20% EtOAc/petroleum) to give 38 (670 mg, 84% yield) as a light yellow solid. mp 81.3-83.3° C.; $^1$H NMR (400 MHz, CDCl$_3$) δ 2.45 (s, 3H), 3.78 (s, 3H), 3.80 (s, 3H), 5.89 (t, J=2.8 Hz, 1H), 6.26 (d, J=2.8 Hz, 1H), 6.41 (d, J=3.6 Hz, 1H), 6.74 (s, 1H), 6.85 (s, 1H), 6.98 (d, J=8.0

Hz, 1H), 7.12-7.19 (m, 3H), 7.37 (d, J=7.6 Hz, 3H), 7.65 (d, J=3.2 Hz, 1H), 7.96 (d, J=8.0 Hz, 2H) ppm; $^{13}$C NMR (CDCl$_3$, 100 MHz) δ 21.68, 55.81, 55.85, 107.74, 108.17, 109.43, 111.60, 116.43, 116.63, 123.90, 125.74, 128.13, 128.36, 128.36, 129.29, 129.66, 129.66, 130.63, 131.01, 131.61, 132.13, 132.77, 133.06, 133.83, 134.05, 134.15, 135.56, 145.37, 145.37, 157.06, 157.69, 182.04, 183.06 ppm; HRMS (M+H$^+$) calcd for C$_{33}$H$_{25}$F$_6$N$_2$O$_6$S, 691.1338. found 691.1336; IR (KBr) 3633, 3433, 3148, 2940, 1650, 1586, 1461, 1413, 1330, 1175, 1129, 1028, 671 cm$^{-1}$.

Synthesis of 1'H-1,3'-Bipyrrole-2,2'-diylbis((2-methoxy-4-(trifluoromethyl)phenyl)methanone) (39)

To a solution of 38 (670 mg, 0.97 mmol) in a 1:1 mixture of MeOH/THF (10 mL) was added KOH (218 mg, 3.88 mmol) at room temperature. After being stirred for 15 min, the mixture was adjusted to pH 7.0 with 0.5 N HCl and extracted with EtOAc (10 mL×3). The combined organic layers were dried over anhydrous sodium sulfate, filtered and concentrated in vacuum. The residue was purified by flash column chromatography (33% EtOAc/petroleum) to give 39 (494 mg, 95% yield) as a light yellow solid. mp 75.0-77.0° C.; $^1$H NMR (400 MHz, CDCl$_3$) δ 3.76 (s, 3H), 3.84 (s, 3H), 5.84 (t, J=4.0 Hz, 1H), 6.29-6.32 (m, 2H), 6.65 (s, 1H), 6.87 (s, 1H), 6.95 (d, J=7.6 Hz, 1H), 7.11 (t, J=3.2 Hz, 1H), 7.14 (s, 1H), 7.19-7.21 (m, 2H), 7.25-7.26 (m, 1H), 9.51 (br, s, 1H) ppm; $^{13}$C NMR (CDCl$_3$, 100 MHz) δ 55.61, 55.85, 107.31, 108.26, 109.08, 110.68, 116.64, 116.87, 116.91, 123.92, 124.21, 125.88, 128.88, 129.38, 131.32, 131.63, 131.75, 132.26, 132.50, 132.58, 132.65, 132.92, 156.39, 157.11, 182.18, 182.49 ppm; HRMS (M+H$^+$) calcd for C$_{26}$H$_{19}$F$_6$N$_2$O$_4$ 537.1249. found 537.1238; IR (KBr) 3295, 2943, 1636, 1462, 1413, 1331, 1126, 1076, 928, 829, 742 cm$^{-1}$.

Synthesis of 1'H-1,3'-Bipyrrole-2,2'-diylbis((2-hydroxy-4-(trifluoromethyl)phenyl)methanone) (40)

To a solution of 39 (100 mg, 0.19 mmol) in dry CH$_2$Cl$_2$ (5 mL) was slowly added a solution of BBr$_3$ (233 mg, 0.93 mmol) in dry CH$_2$Cl$_2$ (1 mL) via a syringe under N$_2$ at −78° C. After being stirred for 0.5 h, the mixture was quenched by addition of water (10 mL) and extracted with CH$_2$Cl$_2$ (10 mL×3). The combined organic layers were dried over anhydrous sodium sulfate, filtered and concentrated in vacuum. The residue was purified by flash column chromatography (30% EtOAc/petroleum) to give 40 (78 mg, 82% yield) as a yellow solid. mp 148.0-149.0° C.; $^1$H NMR (400 MHz, CDCl$_3$) δ 6.26 (dd, J=4.0, 2.8 Hz, 1H), 6.39 (s, 1H), 6.69 (d, J=8.0 Hz, 1H), 6.75 (dd, J=4.0, 1.2 Hz, 1H), 6.98 (t, J=2.0 Hz, 1H), 7.01 (d, J=8.4 Hz, 1H), 7.03 (s, 1H), 7.21 (d, J=5.6 Hz, 2H), 7.37 (d, J=8.0 Hz, 1H), 8.40 (d, J=8.0 Hz, 1H), 9.46 (br s, 1H), 10.85 (br s, 1H), 11.42 (br s, 1H) ppm; $^{13}$C NMR (CDCl$_3$, 100 MHz) δ 109.89, 111.00, 114.80, 114.82, 114.83, 114.98, 115.02, 115.42, 115.45, 121.36, 121.80, 123.28, 124.15, 124.47, 129.99, 130.53, 130.92, 132.19, 132.41, 135.85, 136.17, 136.59, 161.01, 162.11, 186.42, 187.09 ppm; HRMS (M+H$^+$) calcd for C$_{24}$H$_{15}$F$_6$N$_2$O$_4$ 509.0936. found 509.0934; IR (KBr) 3334, 3148, 3080, 1636, 1591, 1562, 1412, 1337, 1231, 1130, 1068, 944, 875, 786, 748, 605 cm$^{-1}$.

Synthesis of (4,4',5,5'-tetrachloro-1'H-1,3'-bipyrrole-2,2'-diyl)bis((2-hydroxy-4-(trifluoromethyl)phenyl)methanone) (41)

To a solution of 40 (see supporting information) (50 mg, 0.10 mmol) in dry MeCN (10 mL) at room temperature was stepwise added NCS (72 mg, 0.54 mmol)). After being stirred for about 3.5 h at room temperature, the mixture was quenched with water (10 mL) and extracted with EtOAc (10 mL×3). The combined organic layers were dried over anhydrous sodium sulfate, filtered and concentrated in vacuum. The residue was purified by flash column chromatography (12% EtOAc/petroleum) to give 41 (12 mg, 20% yield) as a yellow solid. mp 70.7-72.3° C.; $^1$H NMR (400 MHz, acetone-d$_6$) δ 6.94 (d, J=8.8 Hz, 1H), 6.97 (s, 1H), 7.07 (s, 1H), 7.19 (s, 1H), 7.27 (d, J=8.8 Hz, 1H), 8.07 (d, J=8.0 Hz, 1H), 8.20 (d, J=8.0 Hz, 1H) ppm; $^{13}$C NMR (DMSO-d$_6$, 100 MHz) δ ppm 110.81, 113.48, 114.92, 115.10, 115.53, 115.93, 120.88, 121.01, 121.34, 121.41, 123.37, 123.49, 125.06, 128.31, 130.63, 132.35, 136.59, 136.92, 137.15, 137.47, 160.50, 162.34, 184.83, 186.07; HRMS (M+H$^+$) calcd for C$_{24}$H$_{11}$C$_{14}$F$_6$N$_2$O$_4$ 644.9377. found 644.9376; IR (KBr) 3789, 3661, 3577, 2917, 2847, 1726, 1636, 1601, 1489, 1407, 1332, 1218, 1133, 946, 832 cm$^{-1}$. HPLC purity, 97.2%.

In Vitro Antibiotic Assays.

A panel of multiple resistance Gram-positive and Gram-negative pathogens listed in Tables 1 and 2 was used to evaluate the antimicrobial activity of marinopyrrole derivatives (Chart 1) with vancomycin as a positive control. Except for those marked with WHO, all pathogens were isolated between 2008 and 2010 in hospitals located in Beijing, Guangzhou, Sichuan, Shandong and Jiangsu Province. Determination of the minimum inhibitory concentration (MIC) was done by the guidelines of the Clinical and Laboratory Standards Institute (Clinical and Laboratory Standards Institute, Performance standards for antimicrobial susceptibility testing, seventeenth informational supplement. 2007, 27, M100-S17). The susceptibility tests of a bacterial strain to a marinopyrrole derivative were performed by an agar dilution method. Briefly, each sterile petri dish contained a final volume of 15 mL comprising 1 mL of a marinopyrrole derivative and 14 mL of Mueller-Hinton broth. The concentrations of a marinopyrrole derivative are 128, 64, 32, 16, 8, 4, 2, 1, 0.5, 0.25, 0.125, 0.06, 0.03, 0.015 and 0.008 μg/mL. The petri dish containing the broth with different concentration of antibiotics was first inoculated with 10$^5$ CFU/mL (Denley A400, United Kingdom) and the culture was then incubated with shaking at 35-37° C. for 18-20 h. The potency of the compound was determined and expressed as minimum inhibitory concentration (MIC) in μg/mL. The MIC was determined as the lowest concentration of antibiotic that inhibited visible bacterial growth.

TABLE 1

In vitro activity of marinopyrrole A and an initial set of derivatives[a]

| Pathogens | No. of isolates | MIC (μg/mL) | | | | | | | | | | | | |
|---|---|---|---|---|---|---|---|---|---|---|---|---|---|---|
| | | 1 | 1c | 1d | 1e | 1f | 1g | 1h | 1i | 1j | 1k | 1m | 1n | Van[b] |
| MSSA[c] | 10 | 0.5-1 | 4-16 | 2-8 | >128 | >128 | >128 | 4-16 | 4-16 | >128 | 8-32 | 2-8 | >64 | 0.5-1 |
| MRSA[d] | 10 | 1 | 4-16 | 4-8 | >128 | >128 | >128 | >64 | 8-16 | >128 | 32-64 | 2-8 | >64 | 0.25-0.5 |

TABLE 1-continued

In vitro activity of marinopyrrole A and an initial set of derivatives[a]

| Pathogens | No. of isolates | MIC (μg/mL) | | | | | | | | | | | | |
|---|---|---|---|---|---|---|---|---|---|---|---|---|---|---|
| | | 1 | 1c | 1d | 1e | 1f | 1g | 1h | 1i | 1j | 1k | 1m | 1n | Van[b] |
| MRSE[e] | 3 | 0.06-1 | 2-4 | 0.5-4 | >128 | >128 | >128 | 0.13-1 | 0.25-4 | >128 | 0.03-4 | 0.25-4 | >64 | 0.13-0.5 |
| VRE (WHO-3)[f] | 1 | 0.5-1 | 2 | 2 | >128 | >128 | >128 | 4 | 4 | >128 | 8 | 0.5 | >64 | >64 |
| ORSA (WHO-25)[g] | 1 | 1 | 8 | 4 | >128 | >128 | >128 | 4 | 8 | >128 | 8 | 4 | >64 | 2 |
| MRSA (WHO-31)[h] | 1 | 1 | 4 | 4 | >128 | >128 | >128 | 4 | 4 | >128 | 8 | 4 | >64 | 0.5 |
| VRE[i] | 2 | 16-128 | >128 | >128 | >128 | >128 | >128 | >128 | >128 | >128 | >128 | >128 | >64 | >128 |
| K. penumonia | 4 | | | | | | | | | | | | | |
| P. aeruginosa | 4 | >128 | >128 | >128 | >128 | >128 | >128 | >128 | >128 | >128 | >128 | >128 | >64 | >128 |
| E. coli | 4 | | | | | | | | | | | | | |

Compound 1 is marinopyrrole A; [a]Except for those marked with WHO, all pathogens were isolated between July 2008 and October 2009 in hospitals located in Beijing; Guangzhou; Sichuan, Shandong and Jiangsu Province. [b]Vancomycin. [c]Methicillin-susceptible Staphylococcus aureus. [d]Methicillin-resistant Staphylococcus aureus. [e]Methicillin-resistant Staphylococcus epidermidis. [f]Moderately vancomycin-resistant Enterococci faecium with the VanA gene. [g]Oxacillin-resistant Staphylococcus aureus. [h]Methicillin-resistant Staphylococcus aureus with the mec A gene and PBP2a. [i]Highly vancomycin-resistant Enterococci faecalis.

Table 1). Besides forming an internal hydrogen bond with the ketone moiety, the hydroxyl group in 1 probably serves as a hydrogen bond donor rather than a hydrogen bond acceptor when binding to the targets, because compounds 1c, 1g and 1n, which possess a hydrogen bond acceptor, showed significant loss of activity. An electron-withdrawing group seems to be tolerated in the meta- and para-positions of the phenyl ring and the size of the substituent is less important (cf., 1d, 1e, 1f, 1h, 1i, and 1k). Compound 1k, which bears the strong electron-withdrawing group $CF_3$ in the para-position and lacks the key hydroxyl group in the ortho-position, exhibited the most potent activity against

TABLE 2

In vitro activity of marinopyrrole A and new derivatives[a]

| Pathogens | MIC (μg/mL) | | | | | | | | | | | | |
|---|---|---|---|---|---|---|---|---|---|---|---|---|---|
| | 1 | 19 | 24 | 25 | 26 | 27 | 28 | 29 | 30 | 31 | 32 | 41 | Van[b] |
| MSSA[c] | 0.5 | 32 | 2 | 64 | >64 | >64 | >64 | >64 | >64 | >64 | >64 | 0.125 | 1 |
| MRSA[d] | 0.5-1 | 32 | 2 | 32-64 | >64 | >64 | >64 | >64 | >64 | >64 | >64 | 0.125-0.25 | 0.5-1 |
| MRSE[e] | 0.25 | 4-8 | 2-8 | 8 | 8-32 | 8-64 | 8 | 32 | 2-16 | 32-64 | 8-64 | <0.008 | 0.5-1 |
| WHO-3[f] | 1 | 4 | 4 | 2 | 16 | 16 | 4 | 8 | >64 | 32 | 64 | 0.5 | >128 |
| WHO-25[g] | 1 | 8 | 4 | 64 | >64 | >64 | 32 | 32 | >64 | >64 | >64 | 1 | 4 |
| WHO-31[h] | 1 | 8 | 2 | 16 | >64 | >64 | >64 | 64 | >64 | >64 | >64 | 1 | 1 |

Compound 1 is marinopyrrole A; [a]Except for those marked with WHO, all pathogens were isolated in recent 2-3 years from hospitals located in Beijing; Guangzhou; Sichuan, Shandong and Jiangsu Province. [b]Vancomycin. [c]Methicillin-susceptible Staphylococcus aureus., data from 8 isolates. [d]Methicillin-resistant Staphylococcus aureus., data from 8 isolates. [e]Methicillin-resistant Staphylococcus epidermidis., data from 4 isolates. [f]Moderately vancomycin-resistant Enterococci faecium with the VanA gene. [g]Oxacillin-resistant Staphylococcus aureus. [h]Methicillin-resistant Staphylococcus aureus with the mecA gene and PBP2a.

The de-halogenated precursor of 1, which lacks the tetrachloro-substituents on the bispyrrole, exhibited >64 fold lower activity (MIC>32 μg/mL) against the pathogens tested. This result indicates that four chloro atoms on the pyrrole rings play an important role for antibiotic activity. The hydroxyl group in the ortho-position of the phenyl ring is critical. Replacement of the hydroxyl group with other substituents such as H, F, OMe, or $CF_3$ led to lower activity or to a complete loss of activity (cf., 1c, 1d, 1g, 1j and 1n, MRSE compared with the parent compound 1, vancomycin, and other derivatives. Although an electron-donating group in the para-position may reduce potency, compound 1m also bearing a hydroxyl group in the ortho-position, nevertheless showed comparable activities against the tested pathogens MSSA, MRSA, ORSA, MRSE, and VRE when compared with 1. This result reinforces further that the hydroxyl group in the ortho-position of the phenyl ring is pivotal. All compounds are inactive against gram-negative pathogens K. pneumonia, P. aeruginosa, and E. coli.

The parent compound 1 exhibited the potency similar to that of vancomycin against the clinical isolates of methicillin-susceptible Staphylococcus aureus (MSSA), methicillin-resistant Staphylococcus aureus (MRSA), methicillin-resistant Staphylococcus epidermidis (MRSE), and non-clinical isolates of MRSA (WHO-31) and oxacillin-resistant Staphylococcus aureus (ORSA, WHO-25). Design and synthesis of marinopyrrole A derivatives based on the initial results of SAR studies led to novel derivatives 19, 24-32 and 41 with modified chemistries vide supra. Among these derivatives as shown in Table 2, compound 19 showed 4-16 fold decreased potency against MRSA and 2-16 fold against MRSE, respectively, compared with compound 1m. The only structural difference is the para-hydroxyl (19) and para-methoxy (1m) substitution on the phenyl groups. Although this result suggests a hydrogen bond acceptor in the para-position might be favoured, it was not supported by compounds 24-32. Compound 24 bearing the same para-hydroxyl but lacking meta-chloro when compared with 19 exhibited similar potency to that of 1m. Compounds 25-32 with either thioether or sulfone group in the para-positions exhibited no antibiotic activity (MIC>32 µg/mL) against MSSA or MRSA regardless whether with or without the extended functional groups were attached. However, compound 41 (Scheme 4) with a strong electron-withdrawing group, $CF_3$, in the para-position exhibited the most potent antibiotic activity. As shown in Table 2, compound 41 is 8 fold and 4 fold more potent than vancomycin and marinopyrrole A against MSSA, respectively. Compound 41 is also 2-4 fold more potent than both vancomycin and marinopyrrole A against MRSA. Most significantly, compound 41 with MIC of 8 ng/mL is >62 fold and >31 fold more potent than vancomycin and marinopyrrole A against MRSE, respectively.

Further examples of Marinopyrrole derivatives and their effectiveness is shown in Table 3.

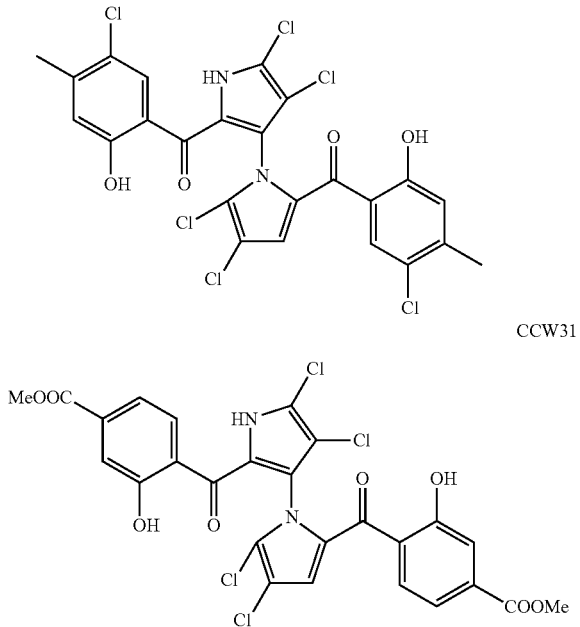

CCW14

CCW31

TABLE 3

In vitro activity of marinopyrrole A and derivatives[a]

| Pathogens | MIC (µg/mL) | | | | |
|---|---|---|---|---|---|
|  | 1 | CCW14 | CCW31 | 41 | Van[b] |
| MSSA[c] | 0.5 | 1 | 1 | 0.125 | 1 |
| MRSA[d] | 0.5-1 | 1 | 1 | 0.125-0.25 | 0.5-1 |
| MRSE[e] | 0.25 | 1 | 0.25-0.5 | <0.008 | 0.5-1 |

TABLE 3-continued

In vitro activity of marinopyrrole A and derivatives[a]

| Pathogens | MIC (µg/mL) | | | | |
|---|---|---|---|---|---|
|  | 1 | CCW14 | CCW31 | 41 | Van[b] |
| WHO-3[f] | 1 | 4 | 2 | 0.5 | >128 |
| WHO-25[g] | 1 | 4 | 2 | 1 | 4 |
| WHO-31[h] | 1 | 1 | 0.5 | 1 | 1 |

Compound 1 is marinopyrrole A;
[a]Except for those marked with WHO, all pathogens were isolated in recent 2-3 years from hospitals located in Beijing; Guangzhou; Sichuan, Shandong and Jiangsu Province.
[b]Vancomycin.
[c]Methicillin-susceptible *Staphylococcus aureus*., data from 8 isolates.
[d]Methicillin-resistant *Staphylococcus aureus*., data from 8 isolates.
[e]Methicillin-resistant *Staphylococcus epidermidis*., data from 4 isolates.
[f]Moderately vancomycin-resistant *Enterococci jaecium* with the VanA gene.
[g]Oxacillin-resistant *Staphylococcus aureus*.
[h]Methicillin-resistant *Staphylococcus aureus* with the mecA gene and PBP2a.

The disclosed symmetrical marinopyrrole derivatives against a panel of gram-positive pathogens including MRSA. The efforts were focused on improving antibiotic potency with chemistry focused on synthetic strategy and route optimization. The methods paved the way towards diverse sets of both symmetrical and potentially asymmetrical marinopyrroles and circumvented the low yields due to the formation of byproduct oxazepine 5 encountered from the first total synthesis.[2] The parent compound, (±)-marinopyrrole A, not only showed potent activity comparable to that of vancomycin against MRSA and MRSE, but it also exhibited higher potency (128-256 fold) than vancomycin against moderately resistant VRE (Table 1). SAR studies of derivatives have clearly demonstrated that the tetrachloro substituents on the pyrrole rings, the hydroxyl group in the ortho position and an electron-withdrawing group in the meta or para position on the phenyl rings are important for achieving potent antibacterial activity against the gram-positive pathogens tested. Of particular interests, the best compound 41 showed 63-125 fold, 8 fold and 4-8 fold more potent than vancomycin, in addition to 31×, 4× and 4× more potent than the parent marinopyrrole A (1), against MRSE, MSSA and MRSA, respectively (Table 3). These results provide useful information for further optimization in the search for new-generation antibiotics against MRSA, MRSE and other pathogens. The SAR studies show that compound 41 has superior antibiotic activity to that of vancomycin against a broad spectrum of gram-positive pathogens.

What is claimed is:
1. A compound having the following formula:

S-4 and (+), (−), and (±) isomers, and pharmaceutically acceptable salts and prodrugs thereof, wherein $R^3$ and $R^{3'}$ are the same and are selected from halogen, hydroxyl, cyano, nitro, substituted or unsubstituted amino, substituted or unsubstituted alkyl, substituted or unsubstituted heteroalkyl, substituted or unsubstituted alkenyl, substituted or unsubstituted heteroalkenyl, substituted or unsubstituted alkynyl, substituted or unsubstituted heteroalkynyl, substituted or unsubstituted aryl, substituted or unsubstituted heteroaryl, substituted or unsubstituted alkoxyl, substituted or unsubstituted aryloxyl, and substituted or unsubstituted carboxyl.

2. The compound of claim 1, wherein at least one of $R^3$ and $R^{3'}$ are halogen.

3. The compound of claim 1, wherein at least one of $R^3$ and $R^{3'}$ are OH, O—CH$_3$, O-alkyl, O-heteroalkyl, O-aryl, O-heteroaryl, NH$_2$, NHR$^{16}$, where $R^{16}$ is alkyl heteroalkyl, aryl, or heteroaryl, NH-alkyl, NH-aryl, NH-heteroaryl, and halogen.

4. The compound of claim 1, wherein one or more of $R^3$ and $R^{3'}$ are halogenated alkyl.

5. The compound of claim 1, wherein one of $R^3$ and $R^{3'}$ are hydroxyl.

6. The compound of claim 1, wherein the compound is selected from one of the following compounds:

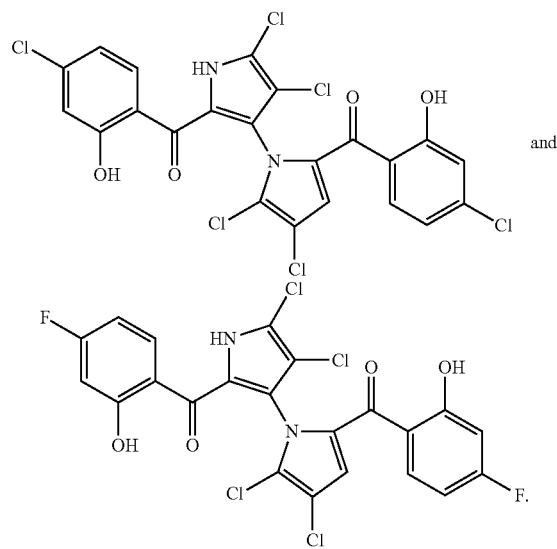

and

7. The compound of claim 1, wherein the compound is

8. A method of treating or reducing a Gram positive bacterial infection in a subject having said infection, comprising administering to the subject, comprising administering to the subject an effective amount of a compound of claim 1.

9. The method of claim 8, wherein the bacterial infection is a *Staphylococcus* infection.

10. The method of claim 8, wherein the bacterial infection is a *Staphylococcus aureus* infection.

11. The method of claim 10, wherein the *Staphylococcus aureus* infection is a methicillin-resistant *Staphylococcus aureus* infection.

12. The method of claim 10, wherein the *Staphylococcus aureus* infection is a hospital-associated methicillin-resistant *Staphylococcus aureus* infection.

13. The method of claim 10, wherein the *Staphylococcus aureus* infection is a community-associated methicillin-resistant *Staphylococcus aureus* infection.

14. The method of claim 8, further comprising administering a second compound, wherein the second compound is an antibacterial compound.

* * * * *